United States Patent
Ohashi et al.

(10) Patent No.: US 11,940,728 B2
(45) Date of Patent: Mar. 26, 2024

(54) MOLECULAR RESIST COMPOSITION AND PATTERNING PROCESS

(71) Applicant: Shin-Etsu Chemical Co., Ltd., Tokyo (JP)

(72) Inventors: Masaki Ohashi, Joetsu (JP); Kazuhiro Katayama, Joetsu (JP); Masahiro Fukushima, Joetsu (JP); Shun Kikuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 185 days.

(21) Appl. No.: 17/484,333

(22) Filed: Sep. 24, 2021

(65) Prior Publication Data

US 2022/0100089 A1   Mar. 31, 2022

(30) Foreign Application Priority Data

Sep. 28, 2020   (JP) .................................. 2020-161573

(51) Int. Cl.
 *G03F 7/004* (2006.01)
 *C07C 59/84* (2006.01)
 (Continued)

(52) U.S. Cl.
 CPC ............ *G03F 7/0045* (2013.01); *C07C 59/84* (2013.01); *C07C 309/71* (2013.01); *C07C 381/12* (2013.01); *C07C 2601/14* (2017.05)

(58) Field of Classification Search
 CPC ............................ G03F 7/0045; C07C 381/12
 See application file for complete search history.

(56) References Cited

U.S. PATENT DOCUMENTS

| 4,533,773 A | 8/1985 | Michaelson et al. |
| 5,064,746 A * | 11/1991 | Schwalm .............. G03F 7/0045 430/326 |

(Continued)

FOREIGN PATENT DOCUMENTS

| JP | H11-102072 A | 4/1999 |
| JP | 2001-194776 A | 7/2001 |

(Continued)

OTHER PUBLICATIONS

Lawson et al., "Effect of acid anion on the behavior of single component molecular resists incorporating ionic photoacid generators", 2009, Microeletronic Engineering, 86, 738-740. (Year: 2009).*

(Continued)

*Primary Examiner* — Chanceity N Robinson
*Assistant Examiner* — Anna Malloy
(74) *Attorney, Agent, or Firm* — WHDA, LLP

(57) ABSTRACT

A molecular resist composition and a pattern forming process. A molecular resist composition comprising a sulfonium salt having a cation of specific structure and an organic solvent has a high sensitivity and forms a resist film with improved resolution and LWR, when processed by EB or EUV lithography. The molecular resist composition does not contain a base polymer. The molecular resist composition comprising a sulfonium salt having a cation of specific partial structure has a high sensitivity and forms a resist film with improved resolution and LWR, so that the resist composition is quite useful for precise micropatterning.

8 Claims, 9 Drawing Sheets

(51) Int. Cl.
*C07C 309/71* (2006.01)
*C07C 381/12* (2006.01)

(56) References Cited

U.S. PATENT DOCUMENTS

| | | | | |
|---|---|---|---|---|
| 5,069,997 A * | 12/1991 | Schwalm | ............... | G03F 7/0045 522/31 |
| 5,069,998 A * | 12/1991 | Schwalm | ............... | G03F 7/0045 430/921 |
| 5,073,474 A * | 12/1991 | Schwalm | ............... | G03F 7/0045 430/905 |
| 5,084,371 A * | 1/1992 | Schwalm | ............... | G03F 7/0045 430/326 |
| 5,159,088 A * | 10/1992 | Schwalm | ............... | C07C 381/12 549/9 |
| 5,191,124 A * | 3/1993 | Schwalm | ............... | C07C 381/12 568/15 |
| 5,300,400 A * | 4/1994 | Schwalm | ............... | G03F 7/0045 430/326 |
| 6,136,500 A * | 10/2000 | Kobayashi | ............ | G03F 7/0382 430/921 |
| 6,294,693 B1 | 9/2001 | Asakawa et al. | | |
| 6,673,511 B1 | 1/2004 | Hatakeyama et al. | | |
| 6,749,988 B2 | 6/2004 | Hatakeyama et al. | | |
| 6,916,593 B2 | 7/2005 | Hatakeyama et al. | | |
| 7,871,751 B2 | 1/2011 | Echigo et al. | | |
| 7,960,091 B2 | 6/2011 | Shimizu et al. | | |
| 9,005,874 B2 | 4/2015 | Komuro et al. | | |
| 9,122,153 B2 | 9/2015 | Echigo et al. | | |
| 9,176,379 B2 | 11/2015 | Ichikawa et al. | | |
| 9,250,518 B2 | 2/2016 | Hatakeyama et al. | | |
| 9,360,753 B2 | 6/2016 | Hatakeyama | | |
| 9,366,960 B2 | 6/2016 | Yamashita et al. | | |
| 9,448,475 B2 | 9/2016 | Masuyama et al. | | |
| 9,563,123 B2 | 2/2017 | Masuyama et al. | | |
| 9,851,637 B2 | 12/2017 | Nagamine et al. | | |
| 10,101,654 B2 | 10/2018 | Hatakeyama et al. | | |
| 10,295,904 B2 * | 5/2019 | Hatakeyama | ......... | G03F 7/2006 |
| 10,303,056 B2 | 5/2019 | Hatakeyama et al. | | |
| 10,474,030 B2 | 11/2019 | Hatakeyama et al. | | |
| 11,604,411 B2 * | 3/2023 | Hatakeyama | ......... | G03F 7/2041 |
| 2003/0152190 A1 | 8/2003 | Watanabe et al. | | |
| 2003/0198894 A1 | 10/2003 | Mizutani et al. | | |
| 2007/0043234 A1 | 2/2007 | Vaultier et al. | | |
| 2007/0083060 A1 * | 4/2007 | Sumino | ................ | C07C 381/12 568/45 |
| 2007/0259773 A1 | 11/2007 | Burdeniuc et al. | | |
| 2009/0311484 A1 * | 12/2009 | McLellan | ............. | G03F 7/0002 252/182.29 |
| 2012/0082936 A1 | 4/2012 | Serizawa et al. | | |
| 2012/0149916 A1 | 6/2012 | Utsumi et al. | | |
| 2012/0208127 A1 | 8/2012 | Hatakeyama | | |
| 2012/0288796 A1 | 11/2012 | Katayama et al. | | |
| 2013/0029270 A1 | 1/2013 | Hatakeyama | | |
| 2013/0052588 A1 | 2/2013 | Yoshida et al. | | |
| 2014/0227636 A1 | 8/2014 | Hirano et al. | | |
| 2014/0242526 A1 | 8/2014 | Allen et al. | | |
| 2015/0086926 A1 | 3/2015 | Ohashi et al. | | |
| 2016/0048076 A1 | 2/2016 | Hatakeyama et al. | | |
| 2017/0097564 A1 | 4/2017 | Nagamine et al. | | |
| 2017/0174801 A1 | 6/2017 | Hirano | | |
| 2017/0184962 A1 | 6/2017 | Hatakeyama et al. | | |
| 2017/0299963 A1 | 10/2017 | Fujiwara | | |
| 2017/0315442 A1 | 11/2017 | Fukushima et al. | | |
| 2017/0351177 A1 * | 12/2017 | Hatakeyama | ......... | G03F 7/0048 |
| 2018/0004087 A1 | 1/2018 | Hatakeyama et al. | | |
| 2018/0081267 A1 | 3/2018 | Hatakeyama et al. | | |
| 2018/0081268 A1 | 3/2018 | Hatakeyama | | |
| 2018/0088463 A1 | 3/2018 | Hatakeyama et al. | | |
| 2018/0101094 A1 | 4/2018 | Hatakeyama et al. | | |
| 2018/0143532 A1 | 5/2018 | Hatakeyama | | |
| 2018/0364570 A1 | 12/2018 | Hatakeyama et al. | | |
| 2018/0373148 A1 | 12/2018 | Hatakeyama et al. | | |
| 2019/0155155 A1 | 5/2019 | Hatakeyama et al. | | |
| 2020/0241414 A1 | 7/2020 | Hatakeyama et al. | | |
| 2020/0241418 A1 | 7/2020 | Hatakeyama | | |
| 2020/0272048 A1 | 8/2020 | Hatakeyama et al. | | |
| 2020/0301274 A1 | 9/2020 | Taniguchi et al. | | |
| 2021/0033970 A1 | 2/2021 | Hatakeyama et al. | | |
| 2021/0033971 A1 | 2/2021 | Hatakeyama | | |
| 2021/0063879 A1 | 3/2021 | Hatakeyama | | |
| 2021/0149301 A1 | 5/2021 | Fujiwara et al. | | |
| 2021/0179554 A1 | 6/2021 | Fujiwara et al. | | |
| 2021/0188770 A1 | 6/2021 | Fujiwara et al. | | |

FOREIGN PATENT DOCUMENTS

| | | |
|---|---|---|
| JP | 2002-226470 A | 8/2002 |
| JP | 2002-363148 A | 12/2002 |
| JP | 2005-326838 A | 11/2005 |
| JP | 2008-133312 A | 6/2008 |
| JP | 2009-145578 A | 7/2009 |
| JP | 2009-181062 A | 8/2009 |
| JP | 2010-061087 A | 3/2010 |
| JP | 2011-39266 A | 2/2011 |
| JP | 2011-039502 A | 2/2011 |
| JP | 2011-530652 A | 12/2011 |
| JP | 2013-025211 A | 2/2013 |
| JP | 2013-83957 A | 5/2013 |
| JP | 2015-90382 A | 5/2015 |
| JP | 2015-108781 A | 6/2015 |
| JP | 2015-161823 A | 9/2015 |
| JP | 2015-172746 A | 10/2015 |
| JP | 2015-180928 A | 10/2015 |
| JP | 5852490 B2 | 2/2016 |
| JP | 2017-219836 A | 12/2017 |
| JP | 2018-4812 A | 1/2018 |
| JP | 2018-49264 A | 3/2018 |
| JP | 2018-060069 A | 4/2018 |
| JP | 2018-97356 A | 6/2018 |
| KR | 10-2012-0093777 A | 8/2012 |
| KR | 10-2012-0127292 A | 11/2012 |
| KR | 10-2016-0019860 A | 2/2016 |
| TW | 201241556 A | 10/2012 |
| TW | 201317707 A | 5/2013 |
| TW | 201516024 A | 5/2015 |
| TW | 201730674 A | 9/2017 |
| WO | 2008/066011 A1 | 6/2008 |
| WO | 2010/059174 A1 | 5/2010 |
| WO | 2013/024777 A1 | 2/2013 |

OTHER PUBLICATIONS

Office Action dated Jun. 20, 2022, issued in counterpart Application No. 110135459. (5 pages).
Lawson et al., "Single Molecule Chemically Amplified Resists Based on Ionic and Non-ionic PAGs", Proc. of SPIE, 2008, vol. 6923, pp. 69230K-1-69230K-10, cited in Specification (10 pages).
Wang et al., "Photobase generator and photo decomposable quencher for high-resolution photoresist applications", Advances in Resist Materials and Processing Technology XXVII, (2010), Proc. of SPIE vol. 7639, pp. 76390W. (15 pages).
Office Action dated Jul. 2, 2018, issued in Korean Application No. 10-2017-0069496 (counterpart to U.S. Appl. No. 15/598,428), with English translation. (12 pages).
Notice of Allowance dated Jun. 29, 2022, issued in U.S. Appl. No. 16/919,574. (13 pages).
Eckert et al., "CIDNP Investigation of Radical Decay Pathways in the Sensitized Photolysis of Triphenylsulfonium Salts", J. Am. Chem. Soc., 1999, 121, 10, pp. 2274-2280. (7 pages).
Office Action dated Feb. 2, 2021, issued in TW Application No. 109127275 (counterpart to U.S. Appl. No. 16/871,648). (10 pages).
Non-Final Office Action dated Mar. 29, 2022, issued in U.S. Appl. No. 16/871,648. (23 pages).
Office Action dated Oct. 15, 2018, issued in TW Application 106134104 (counterpart to U.S. Appl. No. 15/725,404). (9 pages).
Office Action dated Oct. 2, 2018, issued in KR Application No. 10-2017-0128141 (counterpart to U.S. Appl. No. 15/725,404), with English translation. (13 pages).

(56) References Cited

OTHER PUBLICATIONS

Non-Final Office Action dated Mar. 22, 2019, issued in U.S. Appl. No. 15/725,404. (28 pages).
Office Action dated Apr. 16, 2021, issued in TW Application No. 109129970 (counterpart to U.S. Appl. No. 16/984,535). (8 pages).
Non-Final Office Action dated Mar. 30, 2018, issued in U.S. Appl. No. 15/598,428. (17 pages).
Final Office Action dated Aug. 3, 2022, issued in U.S. Appl. No. 16/871,648. (25 pages).

* cited by examiner

MOLECULAR RESIST COMPOSITION AND PATTERNING PROCESS

CROSS-REFERENCE TO RELATED APPLICATION

This non-provisional application claims priority under 35 U.S.C. § 119(a) on Patent Application No. 2020-161573 filed in Japan on Sep. 28, 2020, the entire contents of which are hereby incorporated by reference.

TECHNICAL FIELD

This invention relates to a molecular resist composition and a pattern forming process.

BACKGROUND ART

While a higher integration density, higher operating speed and lower power consumption of LSIs are demanded to comply with the expanding IoT market, the effort to reduce the pattern rule is in rapid progress. The wide-spreading logic device market drives forward the miniaturization technology. As the advanced miniaturization technology, microelectronic devices of 10-nm node are manufactured in a mass scale by the double, triple or quadro-patterning version of the immersion ArF lithography. The experimental mass-scale manufacture of 7-nm node devices by the next generation EUV lithography of wavelength 13.5 nm has started.

In the EUV lithography, chemically amplified resist compositions are applicable to form line patterns to a line width of 20 nm or less. When a polymeric resist composition commonly used in the ArF lithography is used in the EUV lithography, such problems as roughening of pattern surface and difficulty of pattern control arise because the base polymer in the composition has a large molecular size. To overcome the problems, a variety of low-molecular-weight materials are proposed.

Molecular resist compositions are based on low-molecular-weight compounds and free of base polymers commonly used in polymeric resist compositions. The molecular resist composition is expected as one of effective measures for forming small-size patterns. For example, Patent Document 1 discloses a negative tone radiation-sensitive composition adapted for alkaline development, comprising mainly a polyhydric polyphenol compound. Non-Patent Document 1 describes a positive tone resist composition adapted for alkaline development, comprising only an acid generator in the form of a sulfonium salt in which a cation having a tert-butoxycarbonyloxy group attached thereto is combined with a strong acid anion. Since the acid generator has a smaller molecular size than polymers, an improvement in roughness is expectable. However, since the molecular resist composition relying on the chemical amplification mechanism is difficult to control acid diffusion, no satisfactory performance has yet been established. In addition, the EUV resist composition must not only clear roughness, but also provide high sensitivity and resolution at the same time, with further improvements being desired.

One of the causes that retard the development of EUV lithography materials is a small number of photons available with EUV exposure. The energy of EUV is extremely higher than that of ArF excimer laser. The number of photons available with EUV exposure is 1/14 of the number by ArF exposure. The size of pattern features formed by the EUV lithography is less than half the size by the ArF lithography. Therefore, the EUV lithography is quite sensitive to a variation of photon number. A variation in number of photons in the radiation region of extremely short wavelength is shot noise as a physical phenomenon. It is impossible to eliminate the influence of shot noise. Attention is thus paid to stochastics. While it is impossible to eliminate the influence of shot noise, discussions are held how to reduce the influence. There is observed a phenomenon that under the influence of shot noise, values of CDU and LWR are increased and holes are blocked at a probability of one several millionth. The blockage of holes leads to electric conduction failure to prevent transistors from operation, adversely affecting the performance of an overall device.

As the means for reducing the influence of shot noise on the resist side, Patent Document 2 discloses an inorganic resist composition comprising a complex of an element having high EUV absorption. Although the inorganic resist composition has a relatively high sensitivity, it is not yet satisfactory because of outstanding problems including poor solubility in resist solvents, low shelf stability, and defectiveness.

CITATION LIST

Patent Document 1: JP-A 2005-326838 (U.S. Pat. No. 7,871,751)
Patent Document 2: JP-A 2015-108781 (U.S. Pat. No. 9,366,960)
Non-Patent Document 1: Proc. of SPIE Vol. 6923, 69230K (2008)

DISCLOSURE OF INVENTION

An object of the invention is to provide a molecular resist composition which is improved in sensitivity, resolution, and LWR when processed by lithography using high-energy radiation, especially EB or EUV; and a pattern forming process using the resist composition.

The inventors have found that a molecular resist composition comprising a sulfonium salt having a cation of specific partial structure has a high sensitivity and forms a resist film with improved resolution and LWR, so that the resist composition is quite useful for precise micropatterning.

In one aspect, the invention provides a molecular resist composition comprising a sulfonium salt having the formula (1) and an organic solvent.

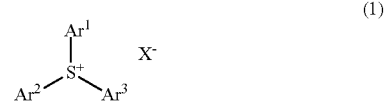

(1)

Herein $Ar^1$, $Ar^2$ and $Ar^3$ are each independently a $C_6$-$C_{20}$ aryl group in which some or all of the hydrogen atoms on its aromatic ring may be substituted by halogen or a $C_1$-$C_{20}$ hydrocarbyl group which may contain a heteroatom, at least one of $Ar^1$, $Ar^2$ and $Ar^3$ is substituted with a group having the formula (1a), (1b) or (1c), any two of $Ar^1$, $Ar^2$ and $Ar^3$ may bond together to form a ring with the sulfur atom to which they are attached.

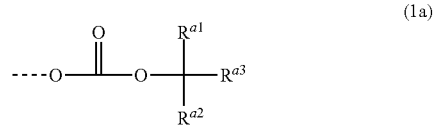

(1a)

-continued

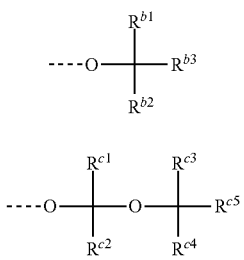
(1b)

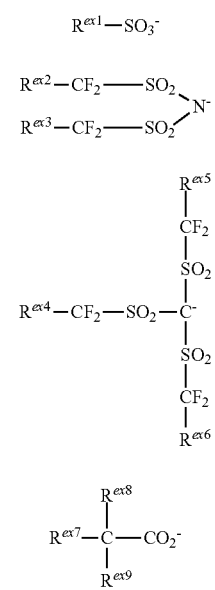
(1c)

wherein $R^{a1}$, $R^{a2}$ and $R^{a3}$ are each independently hydrogen or a $C_1$-$C_{10}$ hydrocarbyl group; $R^{b1}$, $R^{b2}$ and $R^{b3}$ are each independently a $C_1$-$C_{10}$ hydrocarbyl group, $R^{b1}$ and $R^{b2}$ may bond together to form a ring with the carbon atom to which they are attached; $R^{c1}$ and $R^{c2}$ are each independently hydrogen or a $C_1$-$C_{10}$ hydrocarbyl group, $R^{c3}$, $R^{c4}$ and $R^{c5}$ are each independently a $C_1$-$C_{10}$ hydrocarbyl group, $R^{c3}$ and $R^{c4}$ may bond together to form a ring with the carbon atom to which they are attached; the broken line designates a valence bond.

$X^-$ is an anion, exclusive of $BF_4^-$, $PF_6^-$, $SbF_6^-$ and anions having the following formulae (ex1) to (ex4):

$$R^{ex1}-SO_3^- \quad (ex1)$$

$$\begin{array}{c} R^{ex2}-CF_2-SO_2 \\ R^{ex3}-CF_2-SO_2 \end{array} N^- \quad (ex2)$$

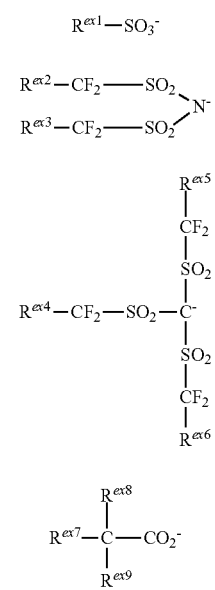
(ex3)

(ex4)

$$R^{ex7}-\underset{R^{ex9}}{\overset{R^{ex8}}{C}}-CO_2^-$$

wherein $R^{ex1}$ is halogen or a $C_1$-$C_{40}$ hydrocarbyl group which may contain a heteroatom; $R^{ex2}$, $R^{ex3}$, $R^{ex4}$, $R^{ex5}$ and $R^{ex6}$ are each independently fluorine or a $C_1$-$C_{40}$ hydrocarbyl group which may contain a heteroatom, $R^{ex2}$ and $R^{ex3}$ may bond together to form a ring with the carbon atoms to which they are attached and intervening atoms, $R^{ex4}$ and $R^{ex5}$ s may bond together to form a ring with the carbon atoms to which they are attached and intervening atoms; $R^{ex7}$ is halogen, hydroxy or a $C_1$-$C_{40}$ hydrocarbyl group which may contain a heteroatom; $R^{ex8}$ and $R^{ex9}$ are each independently fluorine or trifluoromethyl.

In a preferred embodiment, $Ar^1$, $Ar^2$ and $Ar^3$ are a group having the formula (2), (3) and (4), respectively.

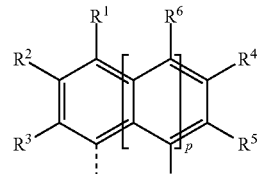
(2)

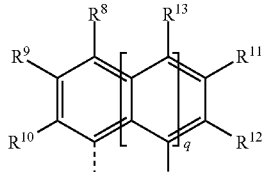
(3)

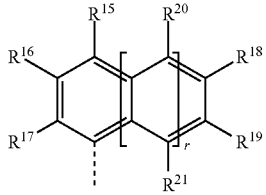
(4)

Herein $R^1$ to $R^{21}$ are each independently hydrogen, hydroxy, cyano, halogen, a $C_1$-$C_{20}$ hydrocarbyl group which may contain a heteroatom, or a group having any one of formulae (1a) to (1c), at least one of $R^1$ to $R^{21}$ being a group having any one of formulae (1a) to (1c), p, q and r are each independently 0 or 1, the broken line designates a valence bond.

In a preferred embodiment, $X^-$ is a halide ion, nitrate ion, hydrogensulfate ion, hydrogencarbonate ion, tetraphenylborate ion, or an anion having any one of the formulae (5) to (8).

(5)

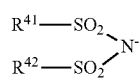
(6)

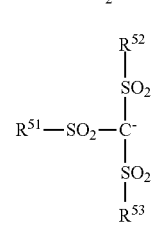
(7)

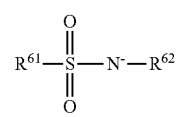
(8)

Herein $R^{31}$ is a $C_1$-$C_{40}$ hydrocarbyl group which may contain a heteroatom, exclusive of a hydrocarbyl group in which hydrogen on α-carbon relative to the carboxy group is substituted by fluorine or trifluoromethyl, $R^{41}$ and $R^{42}$ are each independently a $C_1$-$C_{40}$ hydrocarbyl group which may contain a heteroatom, exclusive of a hydrocarbyl group in which hydrogen on α-carbon relative to the sulfonyl group is substituted by fluorine or trifluoromethyl, $R^{41}$ and $R^{42}$ may bond together to form a ring with the sulfur atoms to which they are attached and intervening atom, $R^{51}$, $R^{52}$ and $R^{53}$ are each independently a $C_1$-$C_{40}$ hydrocarbyl group which may contain a heteroatom, exclusive of a hydrocarbyl group in which hydrogen on α-carbon relative to the sulfonyl group is substituted by fluorine or trifluoromethyl, $R^{51}$ and $R^{52}$ may bond together to form a ring with the sulfur atoms to which they are attached and intervening atom, $R^{61}$ is fluorine or a $C_1$-$C_{10}$ fluorinated hydrocarbyl group which may contain a hydroxy moiety, ether bond or ester bond, $R^{62}$ is hydrogen or a $C_1$-$C_{20}$ hydrocarbyl group which may contain a hydroxy moiety, ether bond or ester bond, $R^{61}$ and $R^{62}$ may bond together to form a ring with the atoms to which they are attached.

The molecular resist composition may further comprise a radical trapping agent and/or a surfactant.

In another aspect, the invention provides a pattern forming process comprising the steps of applying the molecular resist composition defined above to a substrate to form a resist film thereon, exposing the resist film to high-energy radiation, and developing the exposed resist film in a developer. Preferably, the high-energy radiation is EB or EUV.

Advantageous Effects of Invention

The molecular resist composition of the invention meets both high sensitivity and high resolution and is improved in LWR when processed by EB or EUV lithography.

The resist composition is quite useful for precise micropatterning.

DESCRIPTION OF EMBODIMENTS

Figure 1:
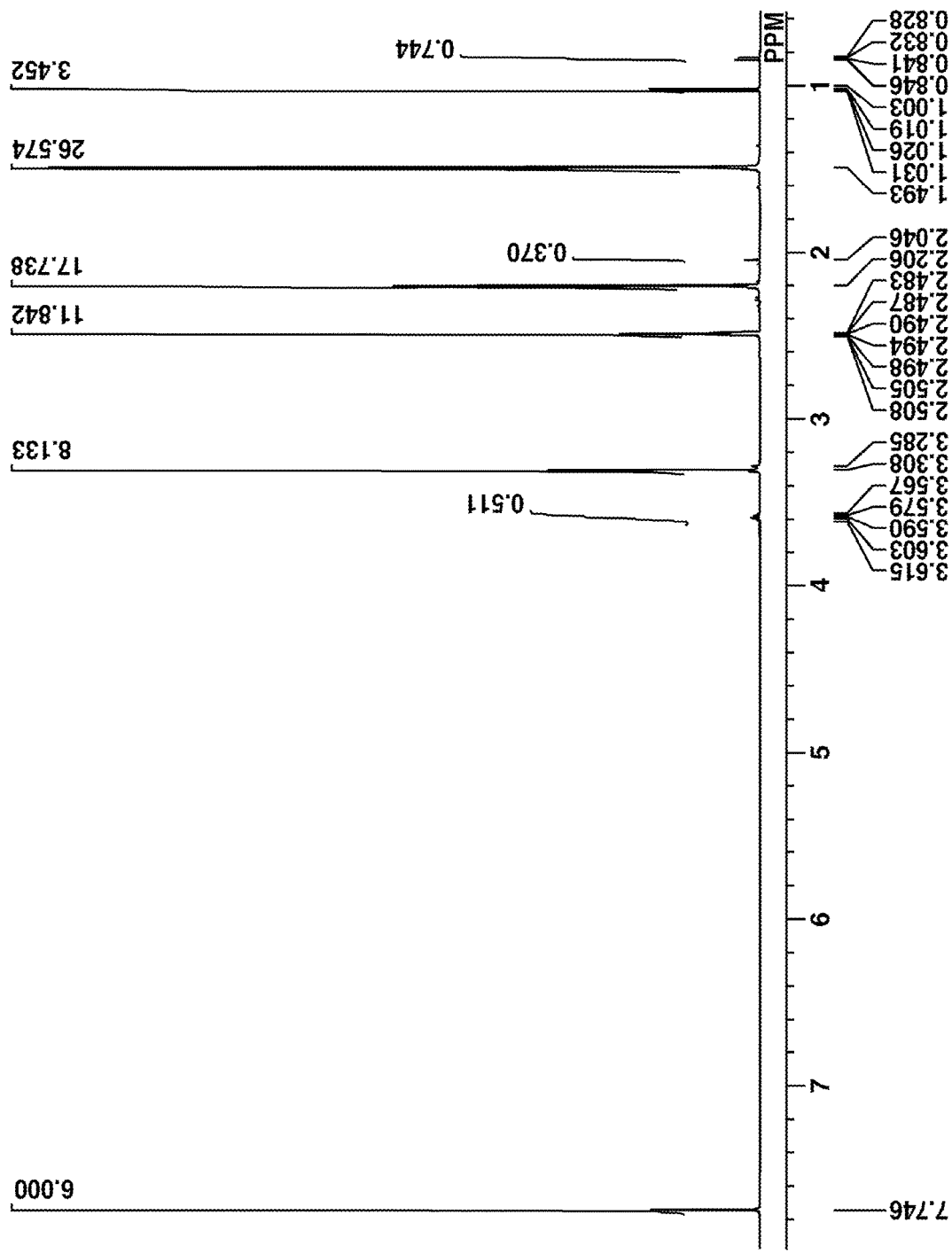
FIG. 1 is a diagram showing the $^1$H-NMR spectrum of sulfonium salt S-1 in Synthesis Example 1.

As used herein, the singular forms "a," "an" and "the" include plural referents unless the context clearly dictates otherwise. The notation (Cn-Cm) means a group containing from n to m carbon atoms per group. In chemical formulae, the broken line designates a valence bond. The terms "group" and "moiety" are interchangeable.

The abbreviations and acronyms have the following meaning.
EB: electron beam
EUV: extreme ultraviolet
PEB: post-exposure bake
PAG: photoacid generator
LWR: line width roughness
CDU: critical dimension uniformity Sulfonium Salt The invention provides a molecular resist composition comprising a sulfonium salt having the following formula (1) as a main component. As used herein, the main component means that the amount of this component is the most in the composition except an organic solvent.

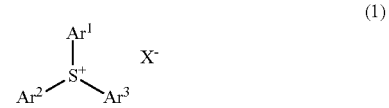

(1)

In formula (1), $Ar^1$, $Ar^2$ and $Ar^3$ are each independently a $C_6$-$C_{20}$ aryl group, at least one of $Ar^1$, $Ar^2$ and $Ar^3$ is substituted with a group having the formula (1a), (1b) or (1c).

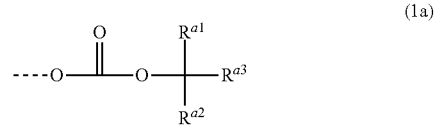

(1a)

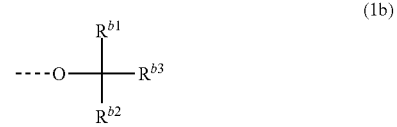

(1b)

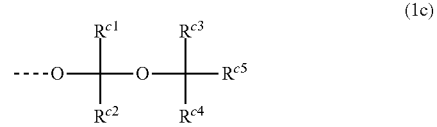

(1c)

In formula (1a), $R^{a1}$, $R^{a2}$ and $R^{a3}$ are each independently hydrogen or a $C_1$-$C_{10}$ hydrocarbyl group. In formula (1b), $R^{b1}$, $R^{b2}$ and $R^{b3}$ are each independently a $C_1$-$C_{10}$ hydrocarbyl group, $R^{b1}$ and $R^{b2}$ may bond together to form a ring with the carbon atom to which they are attached. In formula (1c), $R^{c1}$ and $R^{c2}$ are each independently hydrogen or a $C_1$-$C_{10}$ hydrocarbyl group, $R^{c3}$, $R^{c4}$ and $R^{c5}$ are each independently a $C_1$-$C_{10}$ hydrocarbyl group, $R^{c3}$ and $R^{c4}$ may bond together to form a ring with the carbon atom to which they are attached.

The $C_1$-$C_{10}$ hydrocarbyl group may be saturated or unsaturated and straight, branched or cyclic. Examples thereof include $C_1$-$C_{10}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl and n-decyl; $C_4$-$C_{10}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; $C_2$-$C_{10}$ alkenyl groups such as vinyl and allyl; $C_6$-$C_{10}$ aryl groups such as phenyl and naphthyl, and combinations thereof.

In the hydrocarbyl group, some or all hydrogen may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, halogen, carbonyl, ether bond, thioether bond, ester bond, sulfonic ester bond, carbonate bond, carbamate bond, lactone ring, sultone ring or carboxylic anhydride.

Examples of the group having formula (1a) are given below, but not limited thereto.

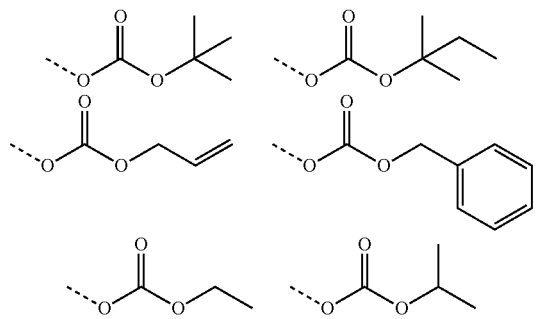

Examples of the group having formula (1b) are given below, but not limited thereto.

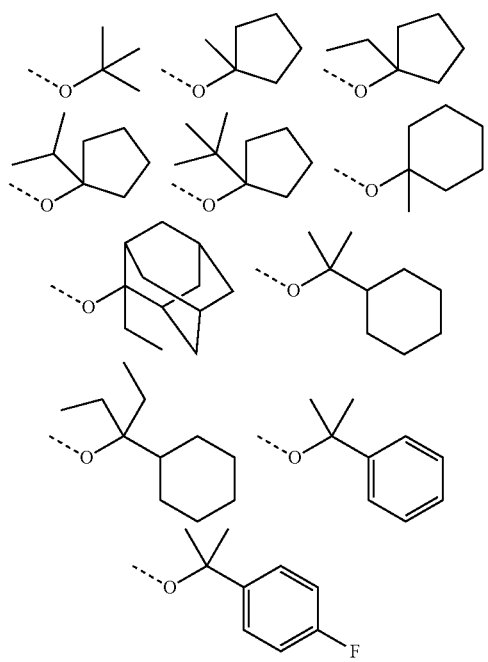

Examples of the group having formula (1c) are given below, but not limited thereto.

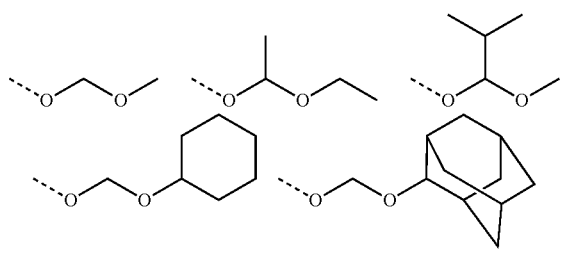

Typical of the $C_6$-$C_{20}$ aryl group represented by $Ar^1$, $Ar^2$ and $Ar^3$ are phenyl and naphthyl. In the aryl group, some or all hydrogen may be substituted by halogen or a $C_1$-$C_{20}$ hydrocarbyl group which may contain a heteroatom.

Suitable halogen atoms include fluorine, chlorine, bromine and iodine. The $C_1$-$C_{20}$ hydrocarbyl group may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; and aryl groups such as phenyl, naphthyl, and anthracenyl. In the hydrocarbyl group, some or all hydrogen may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, halogen, carbonyl, ether bond, thioether bond, ester bond, sulfonic ester bond, carbonate bond, carbamate bond, lactone ring, sultone ring or carboxylic anhydride.

Any two of $Ar^1$, $Ar^2$ and $Ar^3$ may bond together to form a ring with the sulfur atom to which they are attached. Suitable ring structures are shown below, but not limited thereto.

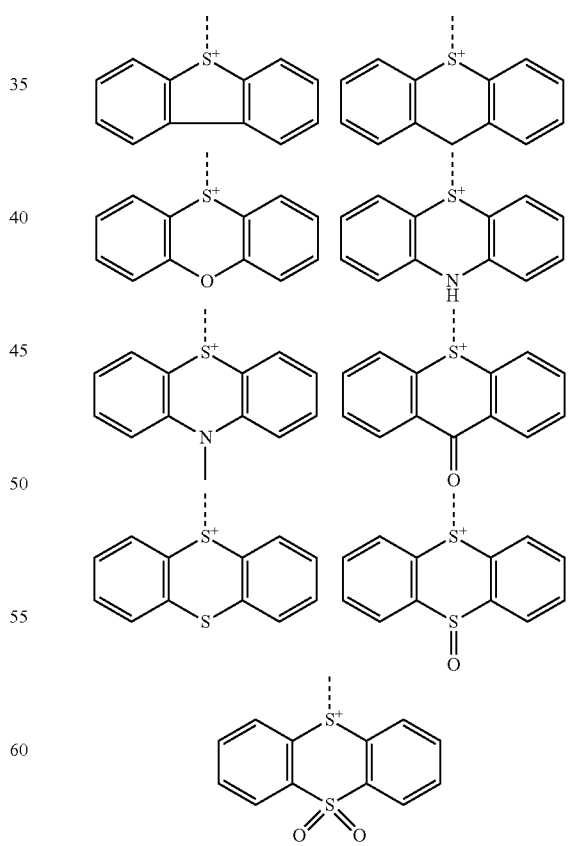

Preferably, $Ar^1$, $Ar^2$ and $Ar^3$ are a group having the formula (2), (3) and (4), respectively.

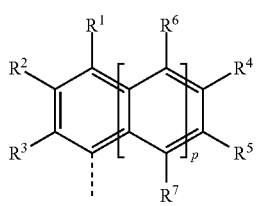
(2)

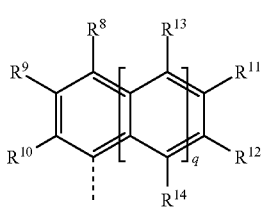
(3)

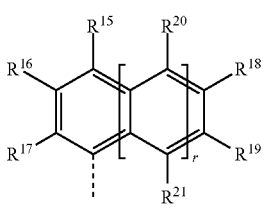
(4)

In formulae (2) to (4), $R^1$ to $R^{21}$ are each independently hydrogen, hydroxy, cyano, halogen, a $C_1$-$C_{20}$ hydrocarbyl group which may contain a heteroatom, or a group having any one of formulae (1a) to (1c). At least one of $R^1$ to $R^{21}$ is a group having any one of formulae (1a) to (1c). The subscripts p, q and r are each independently 0 or 1.

The hydrocarbyl group represented by $R^1$ to $R^{21}$ may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; and aryl groups such as phenyl, naphthyl, and anthracenyl. In the hydrocarbyl group, some or all hydrogen may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, halogen, carbonyl, ether bond, thioether bond, ester bond, sulfonic ester bond, carbonate bond, carbamate bond, lactone ring, sultone ring or carboxylic anhydride. The constituent —CH$_2$— in the hydrocarbyl group may be one attached to a carbon atom on an aromatic ring.

Examples of the cation in the sulfonium salt having formula (1) are shown below, but not limited thereto.

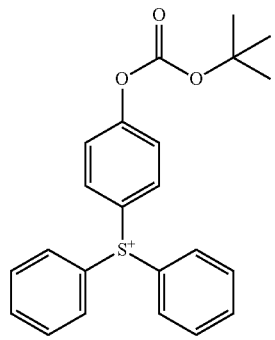

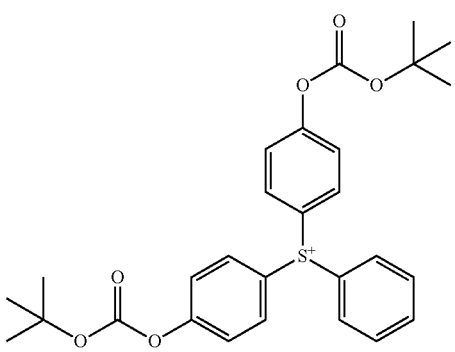

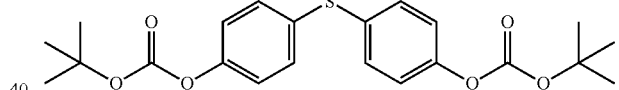

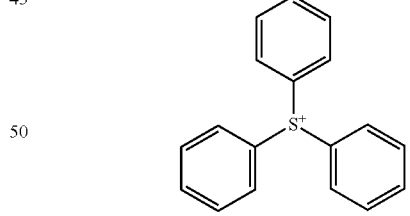

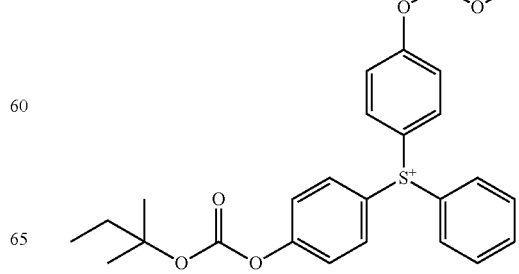

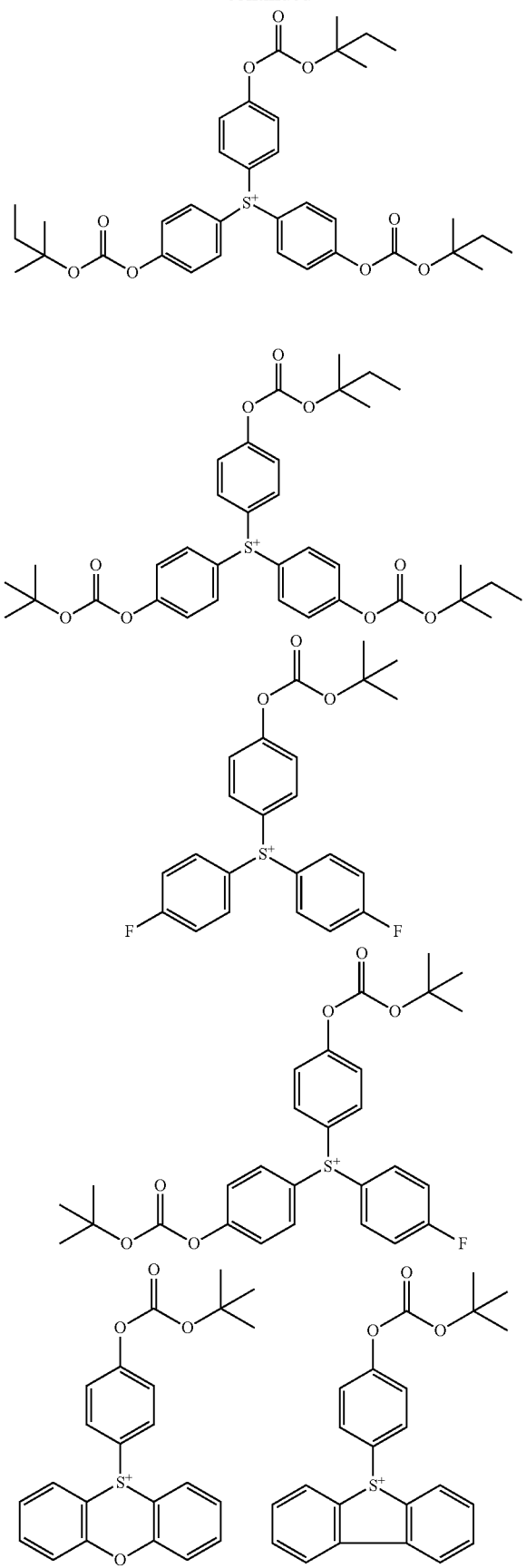
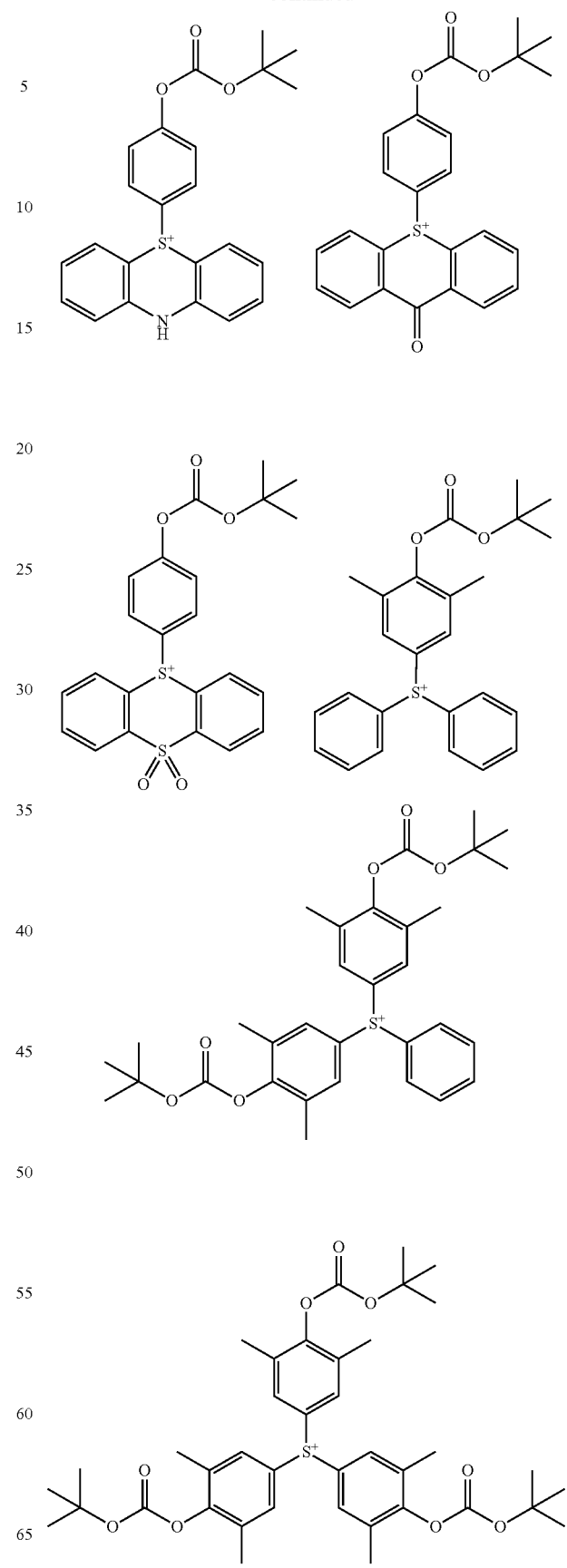

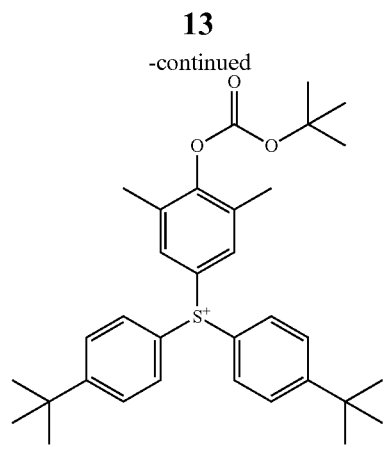
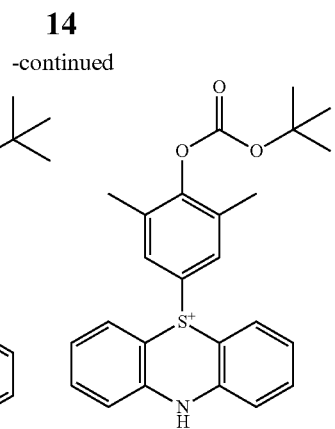
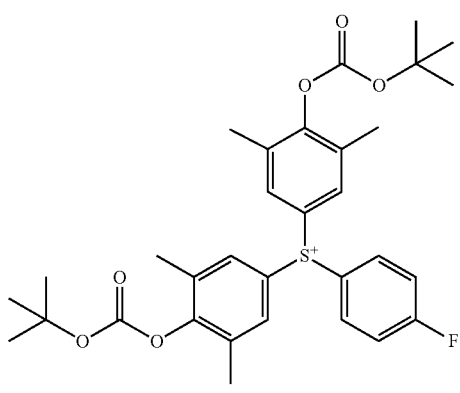
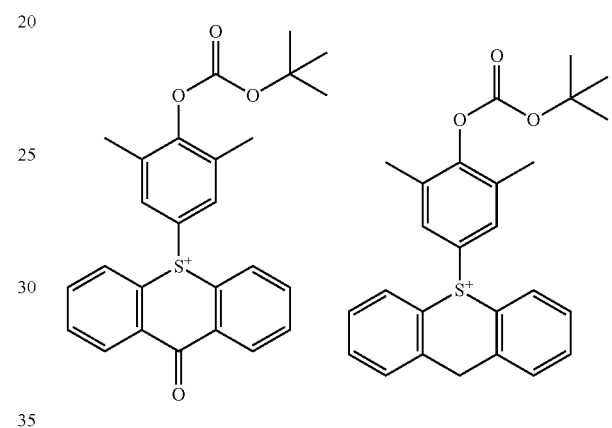
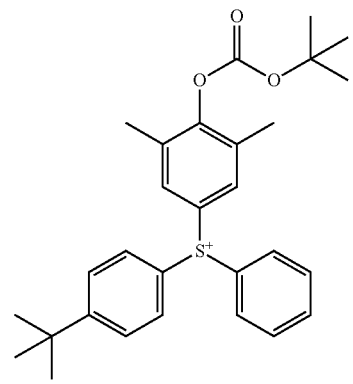
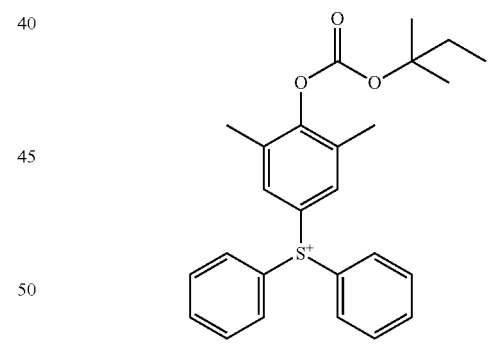
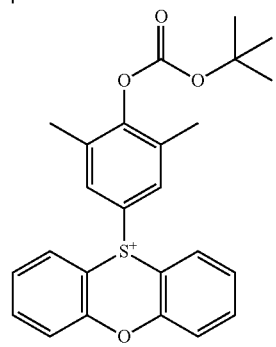
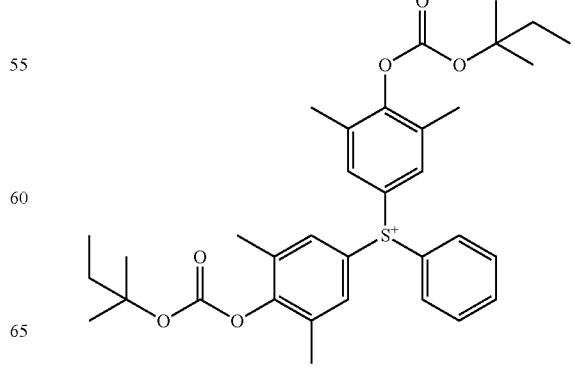

-continued
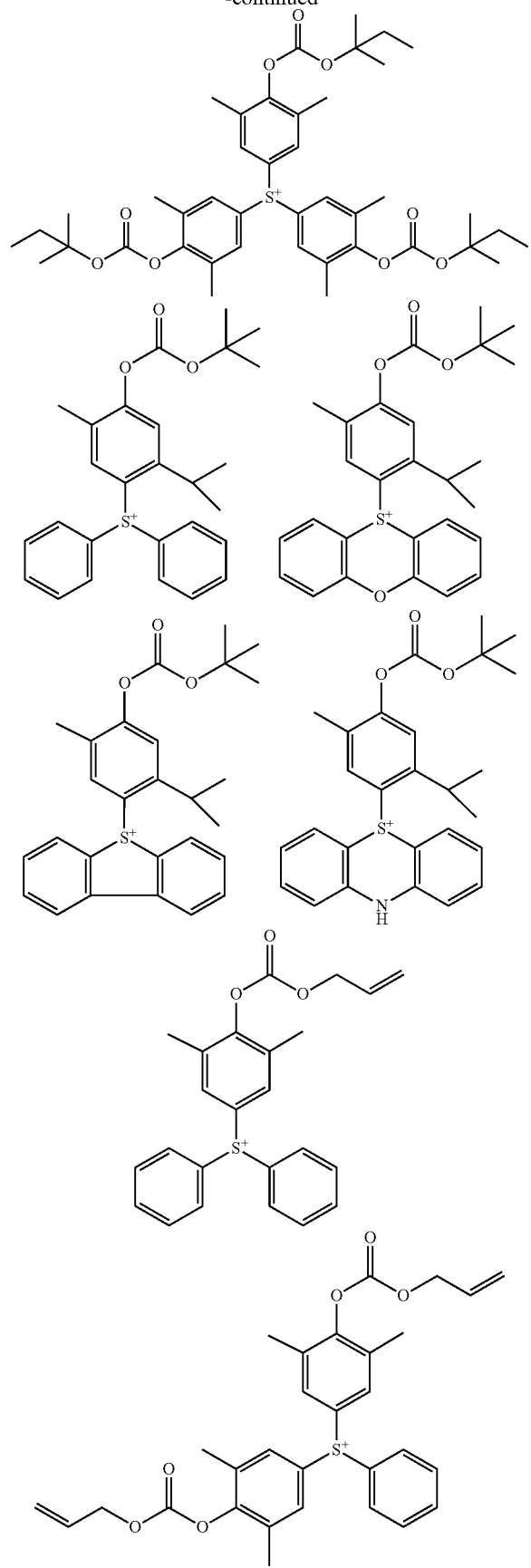
-continued
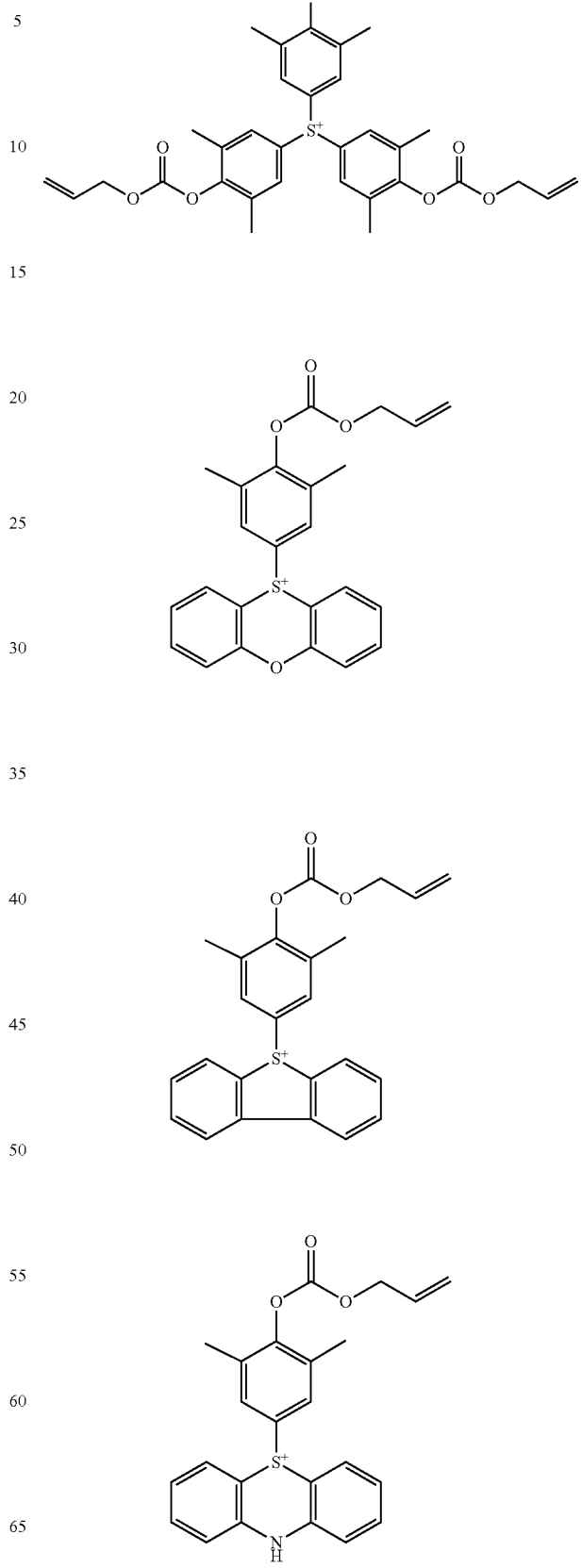

17
-continued
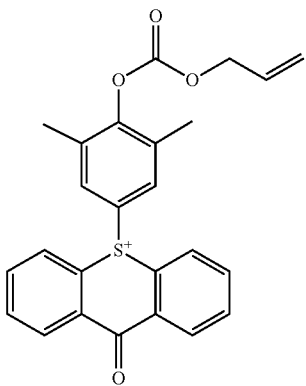
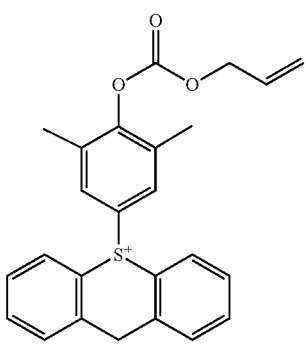
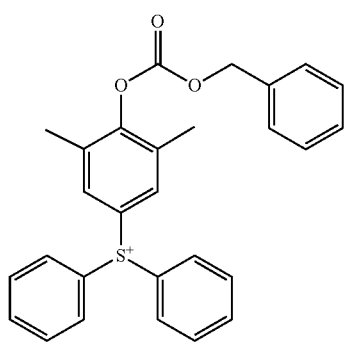
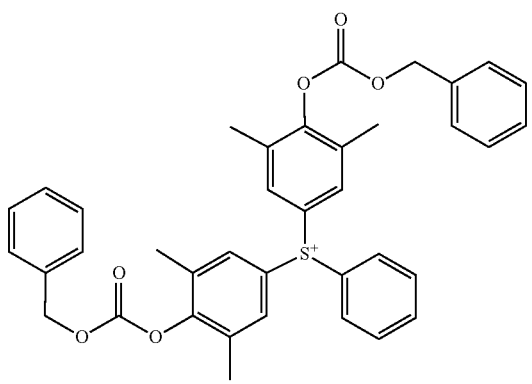
18
-continued
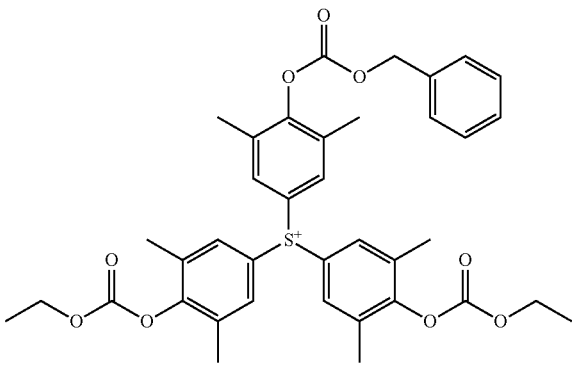
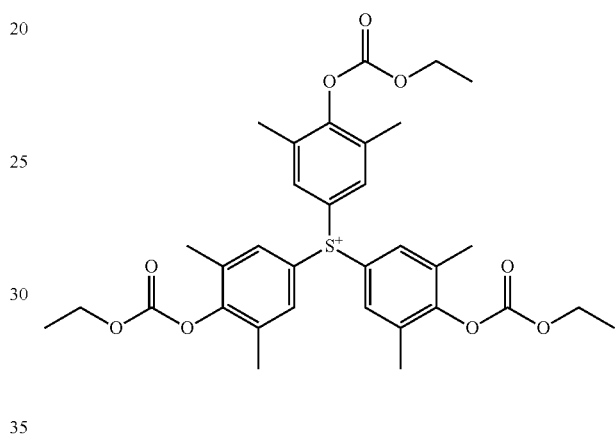
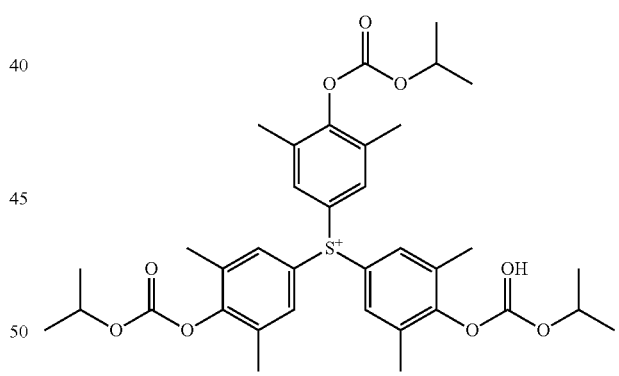
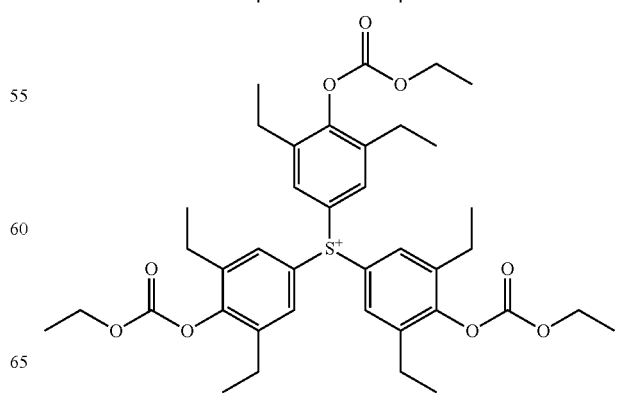

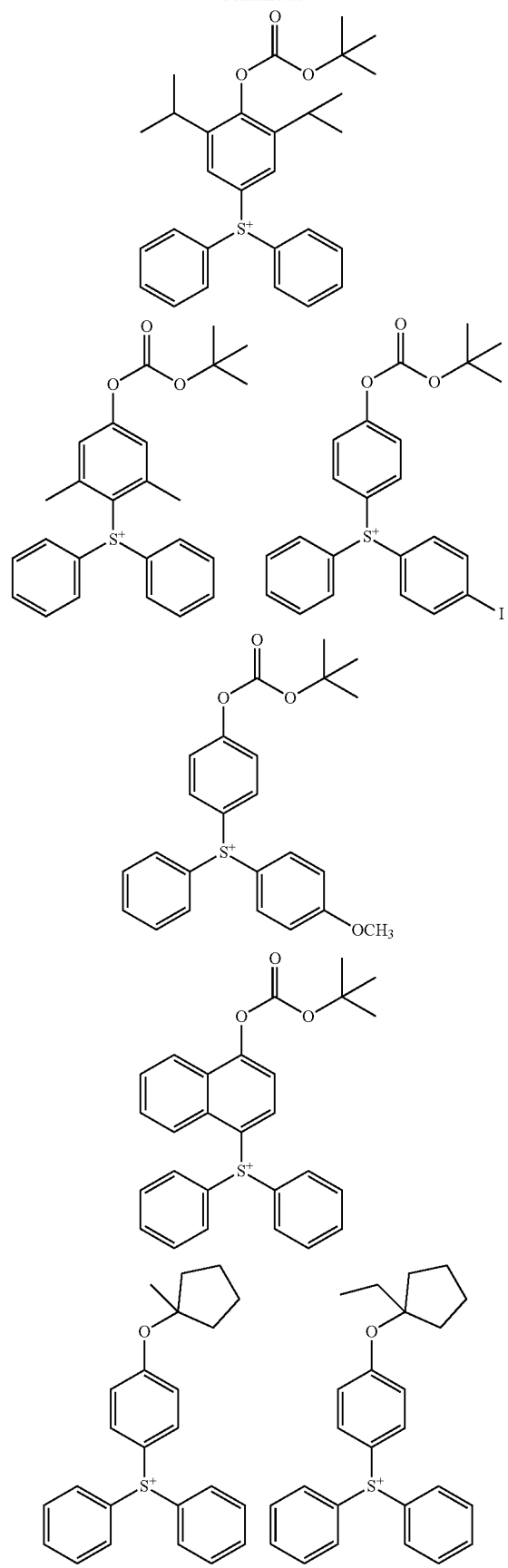
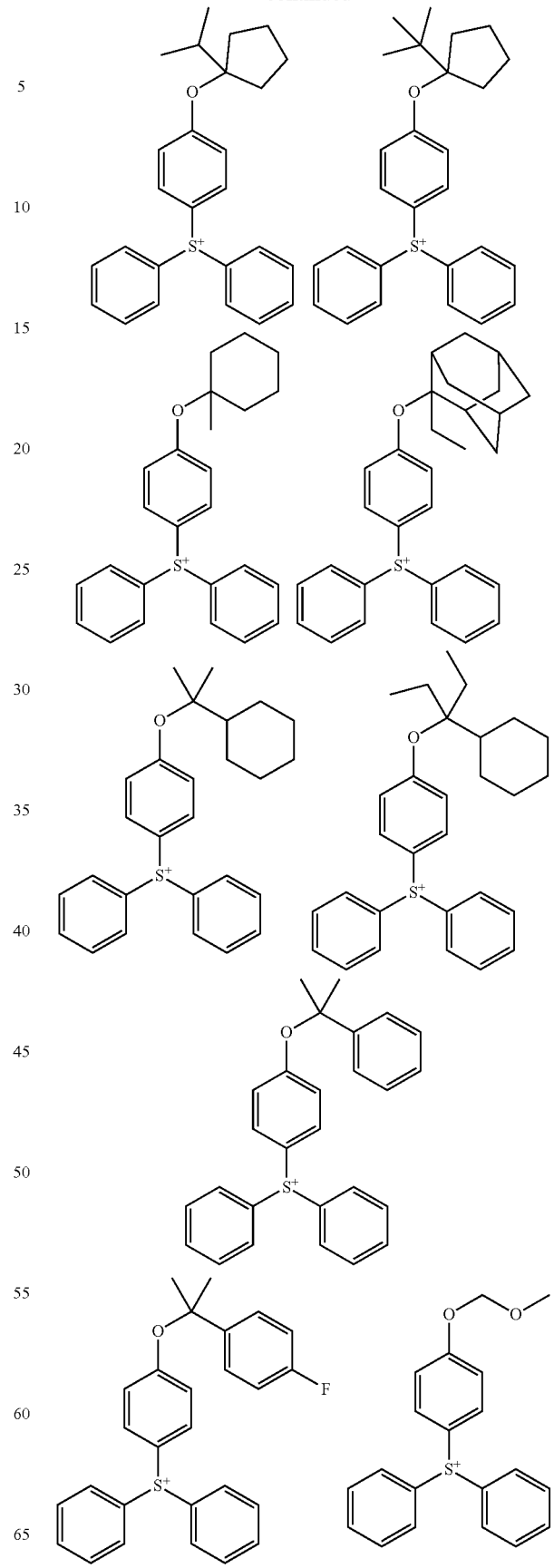

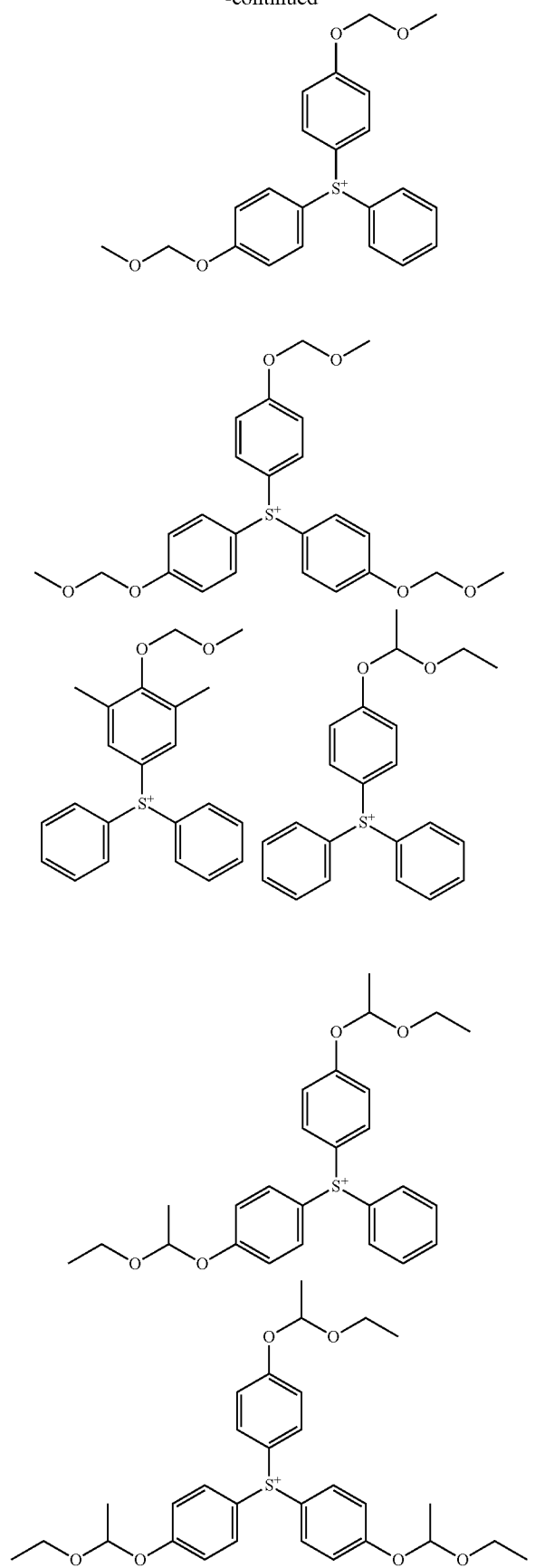
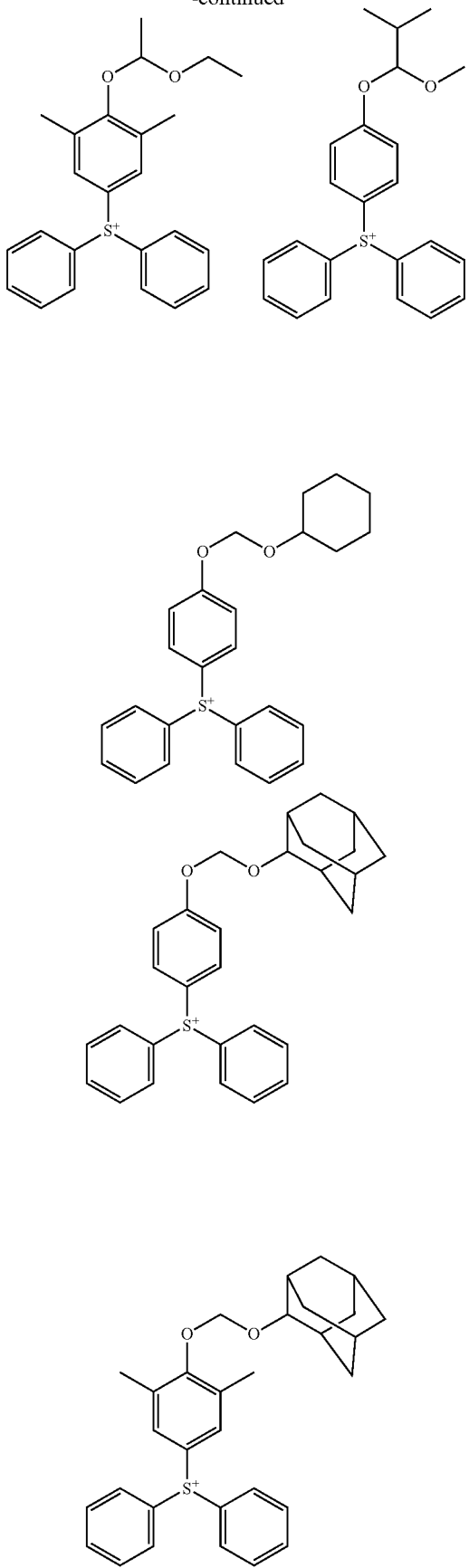

-continued

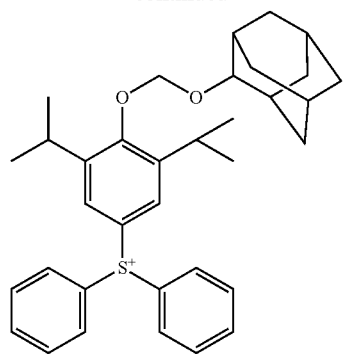

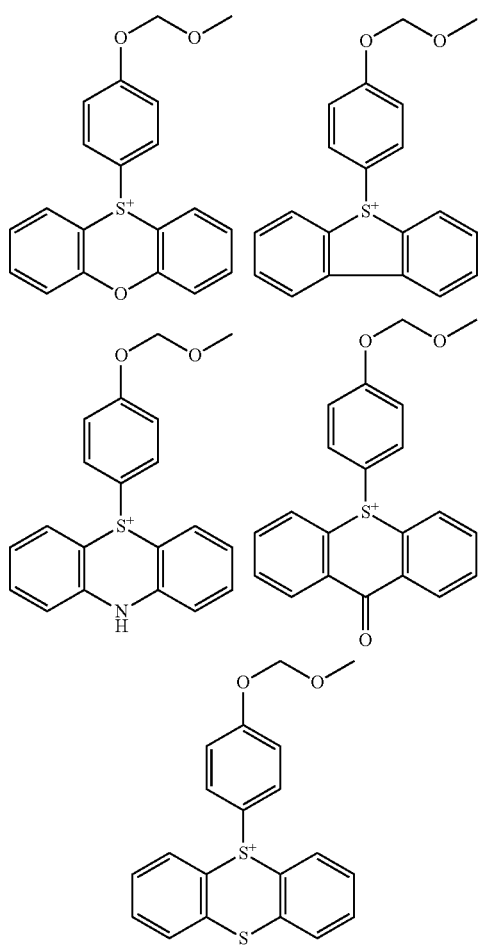

In formula (1), X⁻ is an anion exclusive of $BF_4^-$, $PF_6^-$, $SbF_6^-$ and anions having the following formulae (ex1) to (ex4).

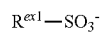
(ex1)

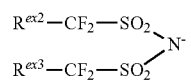
(ex2)

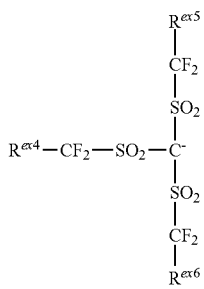
(ex3)

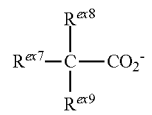
(ex4)

In formulae (ex1) to (ex4), $R^{ex1}$ is halogen or a $C_1$-$C_{40}$ hydrocarbyl group which may contain a heteroatom. $R^{ex2}$, $R^{ex3}$, $R^{ex4}$, $R^{ex5}$ and $R^{ex6}$ are each independently fluorine or a $C_1$-$C_{40}$ hydrocarbyl group which may contain a heteroatom. $R^{ex2}$ and $R^{ex3}$ may bond together to form a ring with the carbon atoms to which they are attached and intervening atoms. $R^{ex4}$ and $R^{ex5}$ may bond together to form a ring with the carbon atoms to which they are attached and intervening atoms. $R^{ex7}$ is halogen, hydroxy or a $C_1$-$C_{40}$ hydrocarbyl group which may contain a heteroatom. $R^{ex8}$ and $R^{ex9}$ are each independently fluorine or trifluoromethyl.

The anion X⁻ is preferably a halide ion, nitrate ion, hydrogensulfate ion, hydrogencarbonate ion, tetraphenylborate ion, or an anion having any one of the formulae (5) to (8), more preferably a halide ion, nitrate ion, or an anion having any one of the formulae (5) to (8).

(5)

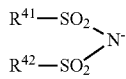
(6)

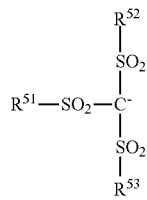
(7)

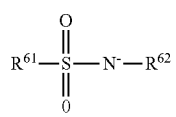
(8)

In formula (5), $R^{31}$ is a $C_1$-$C_{40}$ hydrocarbyl group which may contain a heteroatom, exclusive of a hydrocarbyl group in which hydrogen on α-carbon relative to the carboxy group is substituted by fluorine or trifluoromethyl.

In formula (6), $R^{41}$ and $R^{42}$ are each independently a $C_1$-$C_{40}$ hydrocarbyl group which may contain a heteroatom, exclusive of a hydrocarbyl group in which hydrogen on α-carbon relative to the sulfonyl group is substituted by fluorine or trifluoromethyl. $R^{41}$ and $R^{42}$ may bond together to form a ring with the sulfur atoms to which they are attached and intervening atom.

In formula (7), $R^{51}$, $R^{52}$ and $R^{53}$ are each independently a $C_1$-$C_{40}$ hydrocarbyl group which may contain a heteroatom, exclusive of a hydrocarbyl group in which hydrogen on α-carbon (carbon atom opposite to the methide anion) relative to the sulfonyl group is substituted by fluorine or trifluoromethyl. $R^{51}$ and $R^{52}$ may bond together to form a ring with the sulfur atoms to which they are attached and intervening atom.

In formula (8), $R^{61}$ is fluorine or a $C_1$-$C_{10}$ fluorinated hydrocarbyl group which may contain a hydroxy moiety, ether bond or ester bond. $R^{62}$ is hydrogen or a $C_1$-$C_{20}$ hydrocarbyl group which may contain a hydroxy moiety, ether bond or ester bond. $R^{61}$ and $R^{62}$ may bond together to form a ring with the atoms to which they are attached.

The $C_1$-$C_{40}$ hydrocarbyl group represented by $R^{31}$, $R^{41}$, $R^{42}$, $R^{51}$, $R^{52}$ and $R^{53}$ may be saturated or unsaturated and straight, branched or cyclic. Examples thereof include alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl and n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; aryl groups such as phenyl, naphthyl, and anthracenyl; and combinations thereof. In the hydrocarbyl group, some or all hydrogen may be substituted by a moiety containing a heteroatom such as oxygen, sulfur, nitrogen or halogen, or any constituent —CH$_2$— may be replaced by a moiety containing a heteroatom such as oxygen, sulfur or nitrogen, so that the group may contain a hydroxy, cyano, halogen, carbonyl, ether bond, thioether bond, ester bond, sulfonic ester bond, carbonate bond, carbamate bond, lactone ring, sultone ring or carboxylic anhydride.

The $C_1$-$C_{10}$ fluorinated hydrocarbyl group represented by $R^{61}$ is a $C_1$-$C_{10}$ hydrocarbyl group in which some or all hydrogen is substituted by fluorine. The $C_1$-$C_{10}$ hydrocarbyl group may be saturated or unsaturated and straight, branched or cyclic, and examples thereof are as exemplified above for the $C_1$-$C_{40}$ hydrocarbyl group represented by $R^{31}$, $R^{41}$, $R^{42}$, $R^{51}$, $R^{52}$ and $R^{53}$, but of 1 to 10 carbon atoms.

The $C_1$-$C_{20}$ hydrocarbyl group represented by $R^{12}$ may be saturated or unsaturated and straight, branched or cyclic, and examples thereof are as exemplified above for the $C_1$-$C_{40}$ hydrocarbyl group represented by $R^{31}$, $R^{41}$, $R^{42}$, $R^{51}$, $R^{52}$ and $R^{53}$, but of 1 to 20 carbon atoms.

Examples of the anion having formula (5) are shown below, but not limited thereto.

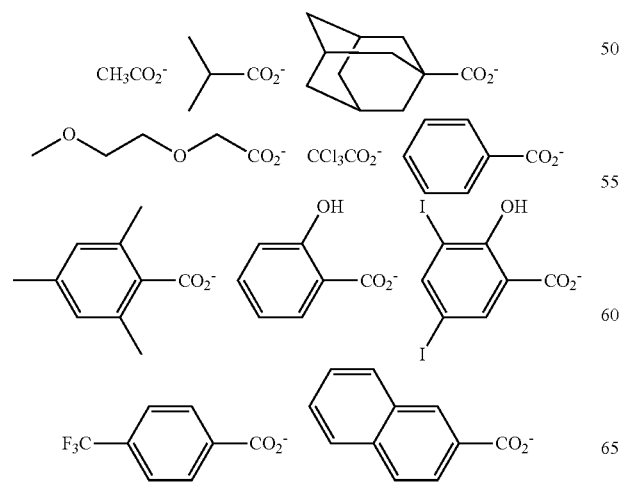

Examples of the anion having formula (6) are shown below, but not limited thereto.

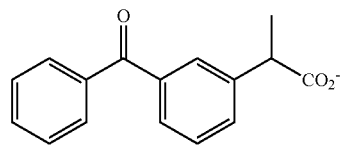

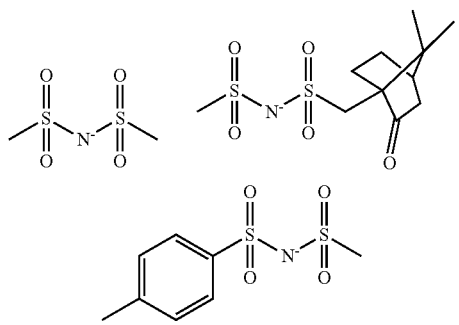

Examples of the anion having formula (7) are shown below, but not limited thereto.

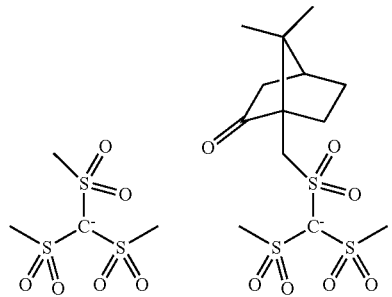

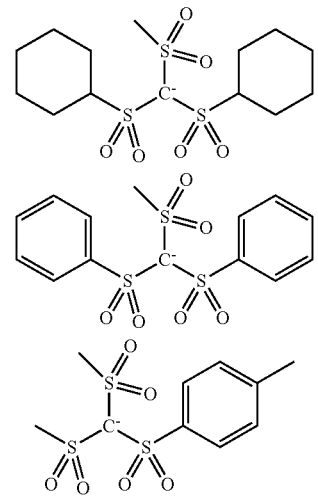

Examples of the anion having formula (8) are shown below, but not limited thereto.

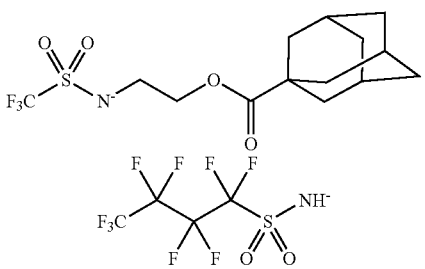

Suitable examples of the sulfonium salt having formula (1) include arbitrary combinations of anions with cations, both as exemplified above.

The sulfonium salt having formula (1) may be used alone or in admixture of two or more. From the standpoint of enhancing the uniformity of component, it is preferred to use the sulfonium salt alone or as a mixture of two.

The sulfonium salt having formula (1) may be synthesized by a suitable combination of well-known organic chemistry procedures. One exemplary procedure is by mixing an onium salt intermediate having a desired cation with an onium salt intermediate having a desired anion, followed by ion exchange reaction. The ion exchange reaction may be performed by a well-known technique, for example, with reference to JP-A 2007-145797.

Organic Solvent

The molecular resist composition of the invention contains an organic solvent. The solvent used herein is not particularly limited as long as it dissolves the sulfonium salt having formula (1) and enables film formation. Suitable organic solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone (GBL), which may be used alone or in admixture.

Of these, 1-ethoxy-2-propanol, PGMEA, cyclohexanone. DAA, GBL, and mixtures thereof are preferred.

An appropriate amount of the organic solvent used is 200 to 5,000 parts by weight per 100 parts by weight of the sulfonium salt having formula (1).

The molecular resist composition of the invention is characterized by comprising the sulfonium salt having formula (1) as a main component and the organic solvent, but not a base polymer. When a resist film formed from the molecular resist composition is exposed to EB or EUV, it forms a negative tone pattern as a result of the exposed region of the resist film turning insoluble in alkaline developer. As used herein, the term "base polymer" refers to a polymer which is a main component of polymeric resist compositions and adapted to change its solubility in developer under the action of an acid generated from an acid generator.

In resist compositions of conventional design, that is, comprising a multiple polymer (or base polymer) as a main component, a photoacid generator, a sensitivity adjusting agent and other additives, it is unlikely that the components are uniformly distributed in a resist film. The non-uniform distribution has a substantial impact on roughness particularly in forming small-size patterns by the EUV lithography. This, combined with the additional influence of the polymer having a large molecular size, causes to degrade LWR and CDU.

In contrast, the molecular resist composition is improved in the uniform distribution of components in a resist film because the composition does not contain a multiple polymer and is of quite simple design. The main component is a low-molecular-weight compound having a small molecular size. LWR and CDU are thus improved particularly in forming small-size patterns by the EB or EUV lithography.

The molecular resist composition enables pattern formation by utilizing a structural change of the sulfonium salt as the main component as a result of photo-reaction. The use of the sulfonium salt having formula (1) brings about a substantial change of solubility in alkaline developer (i.e., insolubilization), forming a negative tone pattern. Since the structural change takes place during exposure, there occurs no acid diffusion as in the case of conventional polymeric chemically amplified resist compositions, that is, image blur due to acid diffusion is eliminated. The resolution performance of the molecular resist composition is better than that of conventional polymeric chemically amplified resist compositions. The molecular resist composition is quite effective in forming small-size patterns.

Although the molecular resist composition does not contain a polymer component functioning as a base polymer, it may contain a polymer component which is used as an additive or which is not a main component, like a polymer serving as a surfactant, as long as the pattern formation by the sulfonium salt having formula (1) is not hindered.

Other Components

The molecular resist composition may contain a radical trapping agent as another component. The addition of a radical trapping agent enables to control photo-reaction during photolithography and adjust sensitivity.

Suitable radical trapping agents include hindered phenols, quinones, hindered amines, and thiol compounds. Exemplary hindered phenols include dibutylhydroxytoluene (BHT) and 2,2'-methylenebis(4-methyl-6-tert-butylphenyl) (Antage W-400 by Kawaguchi Chemical Industry Co., Ltd.). Exemplary quinones include 4-methoxyphenol (Methoquinone by Seiko Chemical Co., Ltd.) and hydroquinone. Exemplary hindered amines include 2,2,6,6-tetramethylpiperidine and 2,2,6,6-tetramethylpiperidine-N-oxy radical. Exemplary thiol compounds include dodecane thiol and hexadecane thiol. When the molecular resist composition contains a radical trapping agent, the amount of the agent is preferably 0.1 to 20 parts, more preferably 0.5 to 10 parts by weight per 100 parts by weight of the sulfonium salt. The radical trapping agent may be used alone or in admixture.

The molecular resist composition may contain a surfactant as a further component. Suitable surfactants include FC-4431 and FC-4430 (3M), PF636, PF656, PF6320, and PF6520 (Omnova Solutions Inc.). When the molecular resist composition contains a surfactant, the amount of the surfactant is preferably 0.001 to 20 parts, more preferably 0.1 to 10 parts by weight per 100 parts by weight of the sulfonium salt. The surfactant may be used alone or in admixture.

Process

Another embodiment of the invention is a pattern forming process using the molecular resist composition defined above. A variety of integrated circuits may be formed from the resist composition using any well-known lithography process. The preferred process includes the steps of applying the molecular resist composition to a substrate to form a resist film thereon, exposing the resist film to high-energy radiation, and developing the exposed resist film in a developer. Any desired steps may be added to the process if necessary.

First, the resist composition is applied to a substrate by a suitable coating technique such as spin coating, roll coating, flow coating, dipping, spraying or doctor coating. The substrate used herein may be a substrate for integrated circuitry fabrication, e.g., Si, $SiO_2$, SiN, SiON, TiN, WSi, BPSG, SOG, organic antireflective film, etc. or a substrate for mask circuitry fabrication, e.g., Cr, CrO, CrON, $MoSi_2$, $SiO_2$, etc. The coating is prebaked on a hot plate preferably at a temperature of 60 to 150° C. for 10 seconds to 30 minutes, more preferably at 80 to 120° C. for 30 seconds to 20 minutes. The resulting resist film preferably has a thickness of 0.01 to 2 μm.

Then the resist film is exposed patternwise to high-energy radiation. Examples of the high-energy radiation include UV, deep UV, EB, EUV, X-ray, soft X-ray, excimer laser, γ-ray, and synchrotron radiation. On use of UV, deep UV, EUV, X-ray, soft X-ray, excimer laser, γ-ray or synchrotron radiation, the resist film is exposed directly or through a mask having a desired pattern, preferably in a dose of 1 to 200 $mJ/cm^2$, more preferably 10 to 100 $mJ/cm^2$. On use of EB, a pattern may be written directly or through a mask having a desired pattern, preferably in a dose of about 0.1 to 100 $\mu C/cm^2$, more preferably about 0.5 to 50 $\mu C/cm^2$. The molecular resist composition is suitable particularly in micropatterning using KrF excimer laser, ArF excimer laser, EB, EUV, X-ray, soft X-ray, γ-ray or synchrotron radiation, especially EB or EUV.

Since the molecular resist composition is adapted to form a pattern or image via a structural change of the sulfonium salt during exposure, the post-exposure bake (PEB) as is necessary for chemically amplified resist compositions is not always necessary. If PEB is involved, the resist film after exposure is baked on a hotplate or in an oven preferably at 30 to 120° C. for 10 seconds to 30 minutes, more preferably at 60 to 100° C. for 30 seconds to 20 minutes.

After the exposure or PEB, the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). In this way, a desired resist pattern is formed on the substrate. Since the molecular resist composition is of negative tone, the exposed region of the resist film is insolubilized and the unexposed region is dissolved away.

After the development in alkaline developer, the resist film is rinsed with pure water and dried by spin drying. Use of a rinse fluid containing a surfactant or supercritical rinsing with carbon dioxide is effective for reducing the stress applied onto the pattern during drying for thereby preventing pattern collapse.

The molecular resist composition may be subjected to negative tone development via organic solvent development to form a negative tone pattern. The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, ethyl phenylacetate, benzyl formate, phenylethyl formate, methyl 3-phenylpropionate, benzyl propionate, and 2-phenylethyl acetate. These organic solvents may be used alone or in admixture of two or more.

At the end of development, the resist film is rinsed if necessary. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene.

Rinsing is effective for minimizing the risks of resist pattern collapse and defect formation. However, rinsing is not essential. If rinsing is omitted, the amount of solvent used may be reduced.

EXAMPLES

Examples of the invention are given below by way of illustration and not by way of limitation. The abbreviation "pbw" is parts by weight. Analysis is made by IR spectroscopy, NMR spectroscopy, and time-of-flight mass spectrometry (TOF-MS) using analytic instruments as shown below.
IR: NICOLET 6700 by Thermo Fisher Scientific Inc.

$^1$H-NMR: ECA-500 by JEOL Ltd.
LC/MS: 6100 series Quadrupole LC/MS system by Agilent Technologies Japan Ltd.

[1] Synthesis of Sulfonium Salts

Synthesis Example 1

Synthesis of tris(4-tert-butoxycarbonyloxy-3,5-dimethylphenyl)sulfonium nitrate (Sulfonium Salt S-1)

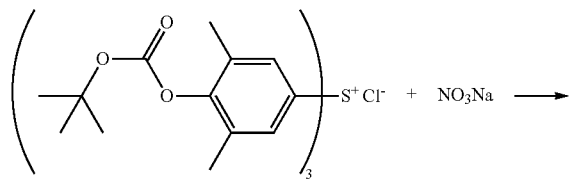

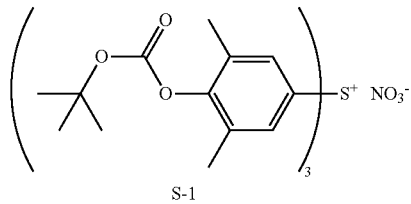

S-1

Synthesis Example 2

Synthesis of tris(4-tert-butoxycarbonyloxy-3,5-dimethylphenyl)sulfonium bis(cyclohexanesulfonyl)(methanesulfonyl)methide (Sulfonium Salt S-2)

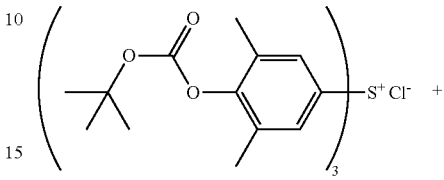

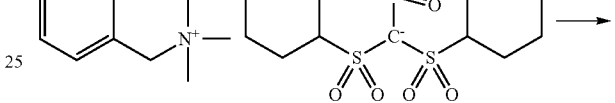

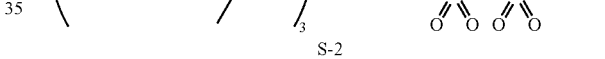

S-2

A mixture of 14.6 g of tris(4-tert-butoxycarbonyloxy-3,5-dimethylphenyl)sulfonium chloride, 6.8 g of sodium nitrate, 65 g of methylene chloride, and 25 g of deionized water was stirred at room temperature for 1 hour. The organic layer was taken out, washed with water, and concentrated under reduced pressure. Methyl isobutyl ketone (MIBK) was added to the concentrate, which was again concentrated under reduced pressure. Diisopropyl ether was added to the residue for recrystallization. The resulting crystals were collected by filtration and dried in vacuum, obtaining 14.2 g (yield 94%) of the target compound, Sulfonium Salt S-1 in powder form. It is noted that the starting reactant, tris(4-tert-butoxycarbonyloxy-3,5-dimethylphenyl)sulfonium chloride was synthesized with reference to Non-Patent Document 1.

Sulfonium Salt S-1 was analyzed by spectroscopy, with the data shown below. FIG. 1 is the $^1$H-NMR/DMSO-$d_6$ spectrum of S-1. In the $^1$H-NMR spectroscopy, residual solvents (diisopropyl ether, MIBK) and water were observed.

IR (D-ATR): 2980, 2932, 1754, 1477, 1458, 1369, 1340, 1272, 1255, 1198, 1141, 1104, 1043, 1012, 897, 861, 593 cm$^{-1}$

MALDI TOF-MS:
  Positive M$^+$ 695 (corresponding to $C_{39}H_{51}O_9S^+$)
  Negative M$^-$ 62 (corresponding to $NO_3^-$)

A mixture of 7.3 g of tris(4-tert-butoxycarbonyloxy-3,5-dimethylphenyl)sulfonium chloride, 5.5 g of benzyltrimethylammonium bis(cyclohexanesulfonyl)(methanesulfonyl)methide, 70 g of methylene chloride, and 30 g of deionized water was stirred at room temperature for 1 hour. The organic layer was taken out, washed with water, and concentrated under reduced pressure. To the concentrate, tert-butyl methyl ether was added for recrystallization. The resulting crystals were collected by filtration and dried in vacuum, obtaining 8.7 g (yield 72%) of the target compound, Sulfonium Salt S-2 in powder form. It is noted that the starting reactant, benzyltrimethylammonium bis(cyclohexanesulfonyl)-(methanesulfonyl)methide was synthesized with reference to JP-A 2020-055797.

Figure 2:
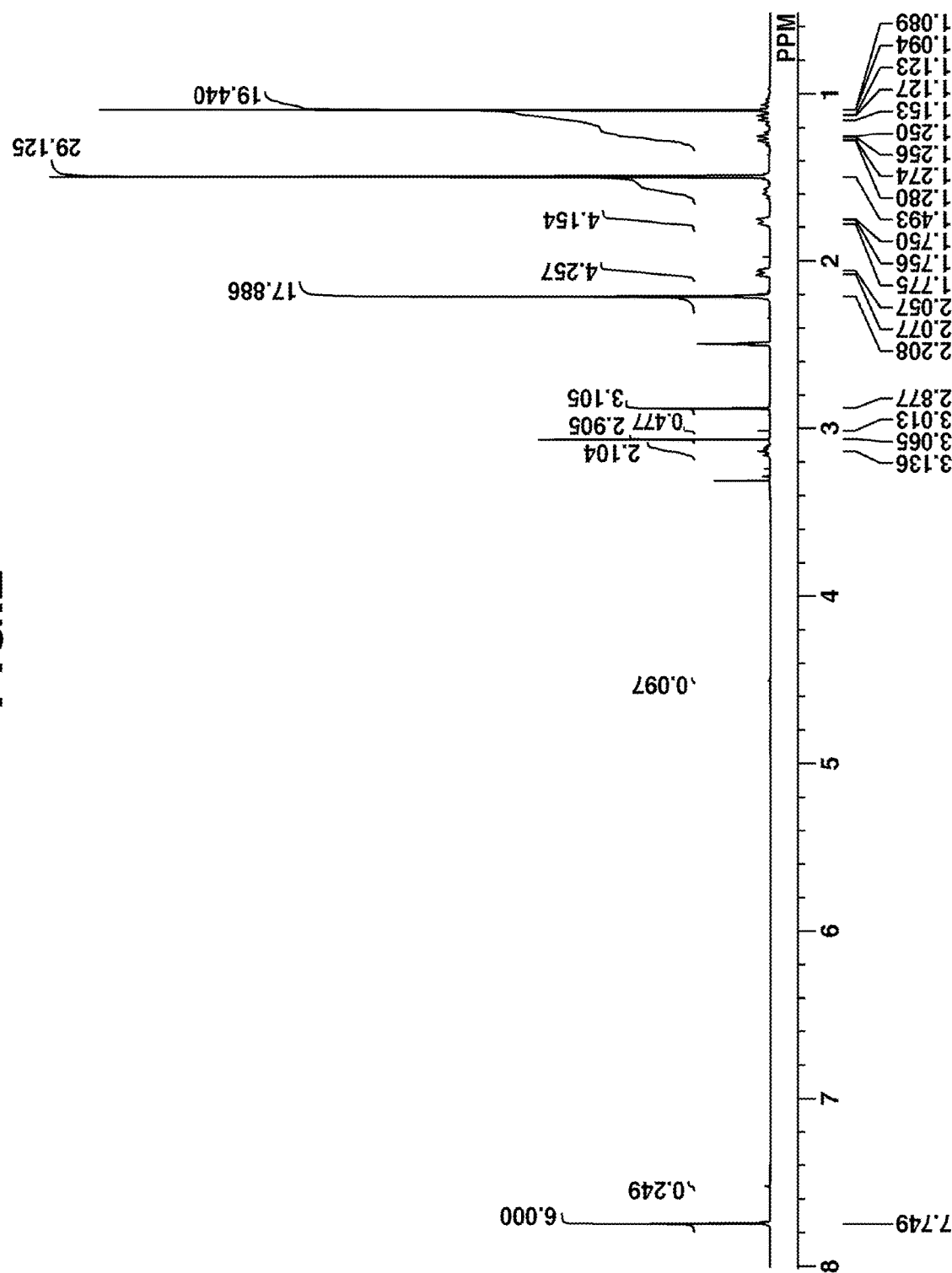
FIG. 2 is a diagram showing the $^1$H-NMR spectrum of sulfonium salt S-2 in Synthesis Example 2.

Sulfonium Salt S-2 was analyzed by spectroscopy, with the data shown below. FIG. 2 is the $^1$H-NMR/DMSO-$d_6$ spectrum of S-2. In the $^1$H-NMR spectroscopy, trace amounts of the reactant benzyltrimethylammonium bis(cyclohexanesulfonyl)(methane-sulfonyl)methide, residual solvent (tert-butyl methyl ether), and water were observed.

IR (D-ATR): 2974, 2932, 2854, 1757, 1477, 1457, 1370, 1287, 1271, 1256, 1200, 1142, 1109, 1012, 990, 897, 863, 608, 544, 528 cm$^{-1}$

MALDI TOF-MS
  Positive M$^+$ 695 (corresponding to $C_{39}H_{51}O_9S^+$)
  Negative M$^-$ 385 (corresponding to $C_{14}H_{25}O_6S_3^-$)

Synthesis Example 3

Synthesis of tris(4-tert-butoxycarbonyloxy-3,5-dimethylphenyl)sulfonium 2-(3-benzoylphenyl)propionate (Sulfonium Salt S-3)

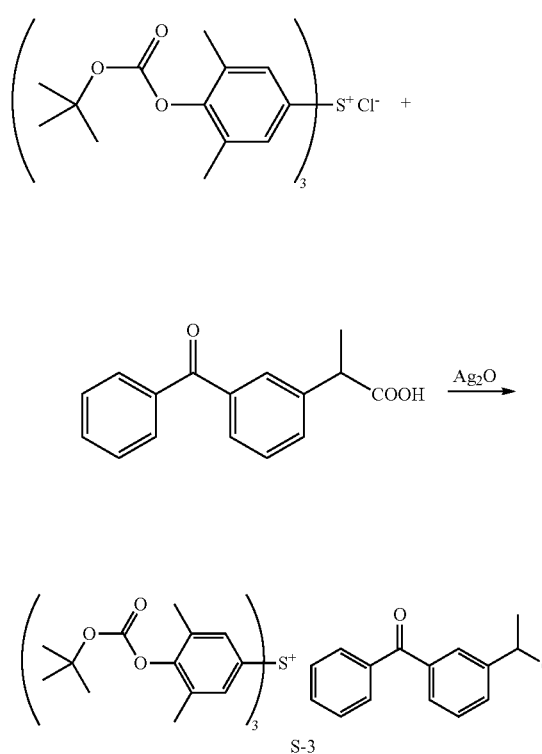

S-3

A mixture of 3.7 g of tris(4-tert-butoxycarbonyloxy-3,5-dimethylphenyl)sulfonium chloride, 1.4 g of 2-(3-benzoylphenyl)propionic acid, 1.2 g of silver (I) oxide, and 30 g of methanol was stirred at 50° C. for 20 hours. The solution was filtered and the filtrate was concentrated under reduced pressure. Methylene chloride, 50 g, was added to the concentrate. The organic layer was washed with saturated sodium hydrogencarbonate water and water, and concentrated under reduced pressure. The solution was purified by silica gel column chromatography, and concentrated under reduced pressure. MIBK was added to the concentrate, which was concentrated again under reduced pressure. Hexane was added to the residue for recrystallization. The resulting crystals were collected by filtration and dried in vacuum, obtaining 2.4 g (yield 51%) of the target compound, Sulfonium Salt S-3 in powder form.

Figure 3:
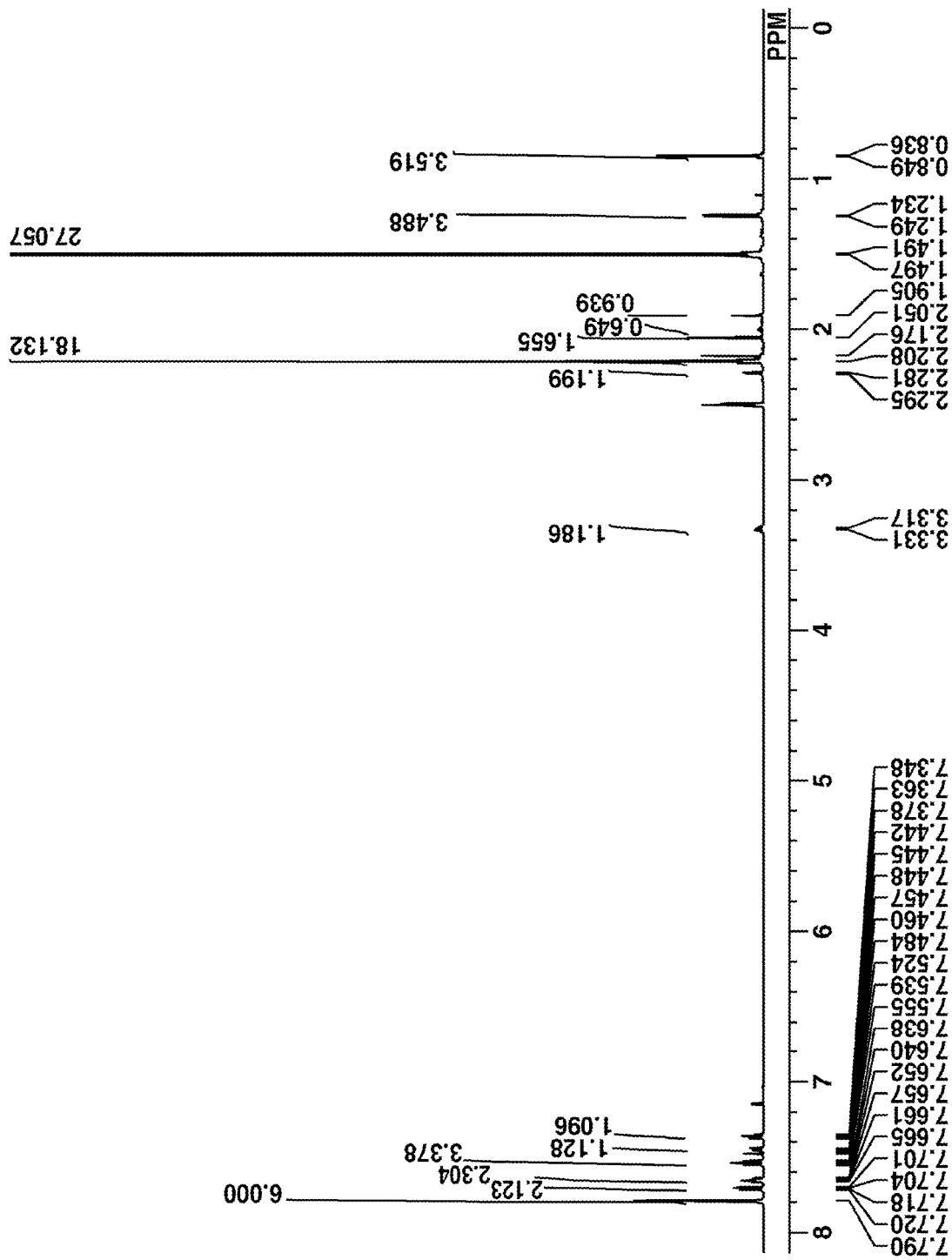
FIG. 3 is a diagram showing the $^1$H-NMR spectrum of sulfonium salt S-3 in Synthesis Example 3.

Sulfonium Salt S-3 was analyzed by spectroscopy, with the data shown below. FIG. 3 is the $^1$H-NMR/DMSO-d$_6$ spectrum of S-3. In the $^1$H-NMR spectroscopy, trace amounts of residual solvent (MIBK) and water were observed.

IR (D-ATR): 2978, 2929, 1756, 1656, 1597, 1578, 1477, 1370, 1317, 1273, 1256, 1196, 1141, 1101, 954, 896, 861, 781, 722, 643, 589 cm$^{-1}$

MALDI TOF-MS

Positive M$^+$ 695 (corresponding to C$_{39}$H$_{51}$O$_9$S$^+$)

Negative M$^-$ 253 (corresponding to C$_{16}$H$_{13}$O$_3^-$)

Synthesis Example 4

Synthesis of tris(4-n-butoxycarbonyloxy-3,5-dimethylphenyl)sulfonium chloride (Sulfonium Salt S-4)

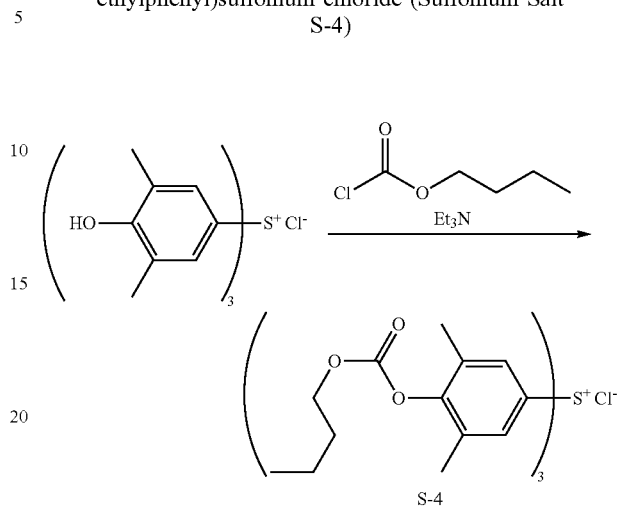

S-4

In 40 g of methylene chloride, 4.3 g of tris(4-hydroxy-3,5-dimethylphenyl)sulfonium chloride, which was synthesized by a well-known method, and 4.9 g of butyl chloroformate were dissolved. Under cooling, 3.6 g of triethylamine was added dropwise to the solution. The solution was stirred at room temperature for 12 hours. After the reaction solution was cooled, 20 g of 5 wt % hydrochloric acid was added dropwise to quench the reaction. The organic layer was taken out, washed with water, and concentrated under reduced pressure. Diisopropyl ether was added to the concentrate for recrystallization. The resulting crystals were collected by filtration and dried in vacuum, obtaining 6.5 g (yield 91%) of the target compound, Sulfonium Salt S-4 in powder form.

Figure 4:
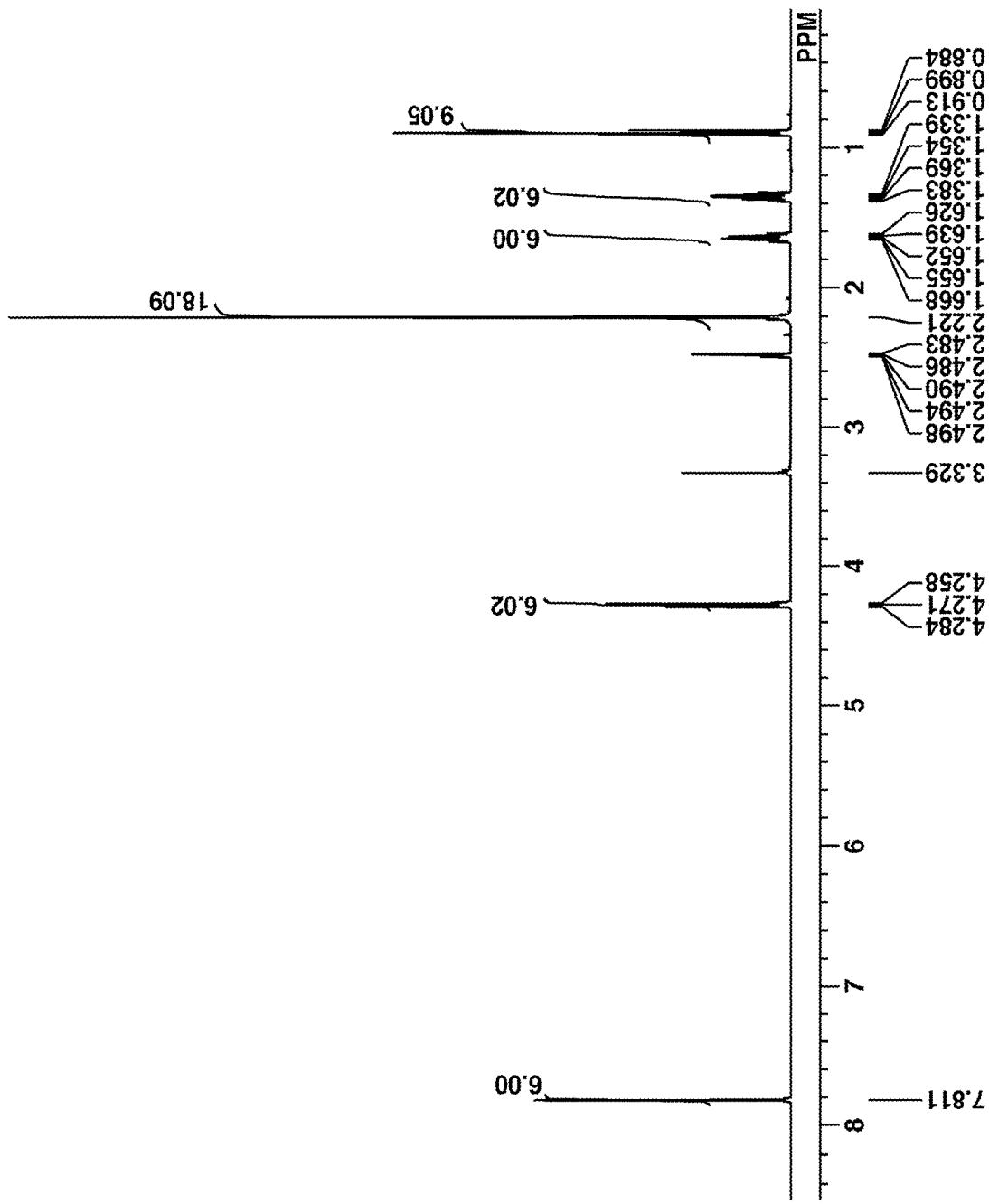
FIG. 4 is a diagram showing the $^1$H-NMR spectrum of sulfonium salt S-4 in Synthesis Example 4.

Sulfonium Salt S-4 was analyzed by spectroscopy, with the data shown below. FIG. 4 is the $^1$H-NMR/DMSO-de spectrum of S-4. In the $^1$H-NMR spectroscopy, a trace amount of water was observed.

IR (D-ATR): 3384, 2962, 2933, 2874, 1761, 1479, 1417, 1390, 1304, 1188, 1110, 1067, 1002, 961, 927, 878, 777, 692, 594, 479 cm$^{-1}$

MALDI TOF-MS

Positive M$^+$ 695 (corresponding to C$_{39}$H$_{51}$O$_9$S$^+$)

Negative M$^-$ 35 (corresponding to Cl$^-$)

Synthesis Example 5

Synthesis of tris(4-n-butoxycarbonyloxy-3,5-dimethylphenyl)sulfonium bis(cyclohexanesulfonyl)(methanesulfonyl)methide (Sulfonium Salt S-5)

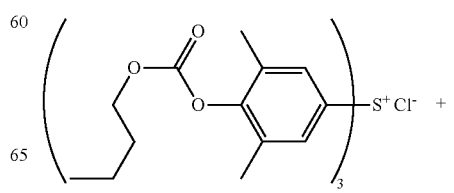

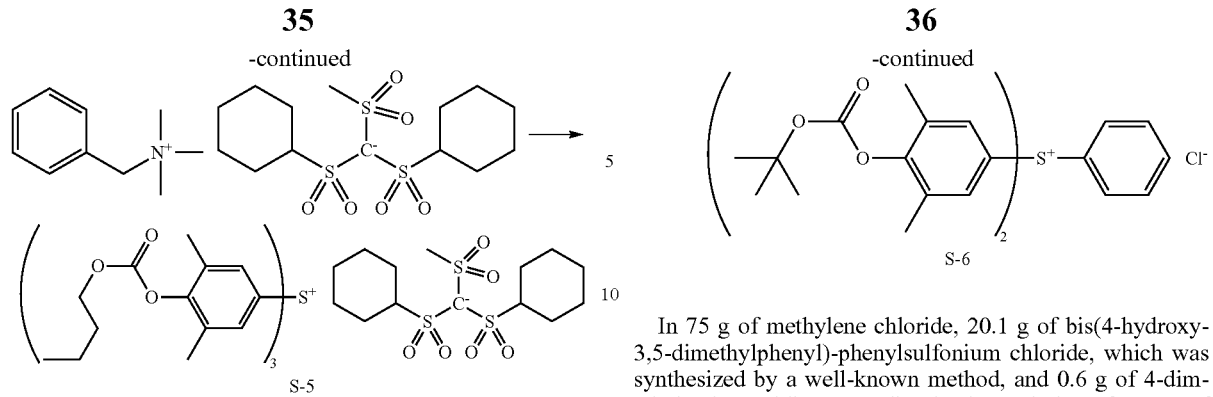

Synthesis was carried out by the same procedure as in Synthesis Example 2 aside from using Sulfonium Salt S-4 instead of tris(4-tert-butoxycarbonyloxy-3,5-dimethylphenyl)sulfonium chloride, obtaining 8.8 g (yield 84%) of the target compound, Sulfonium Salt S-5 as oily mass.

Figure 5:
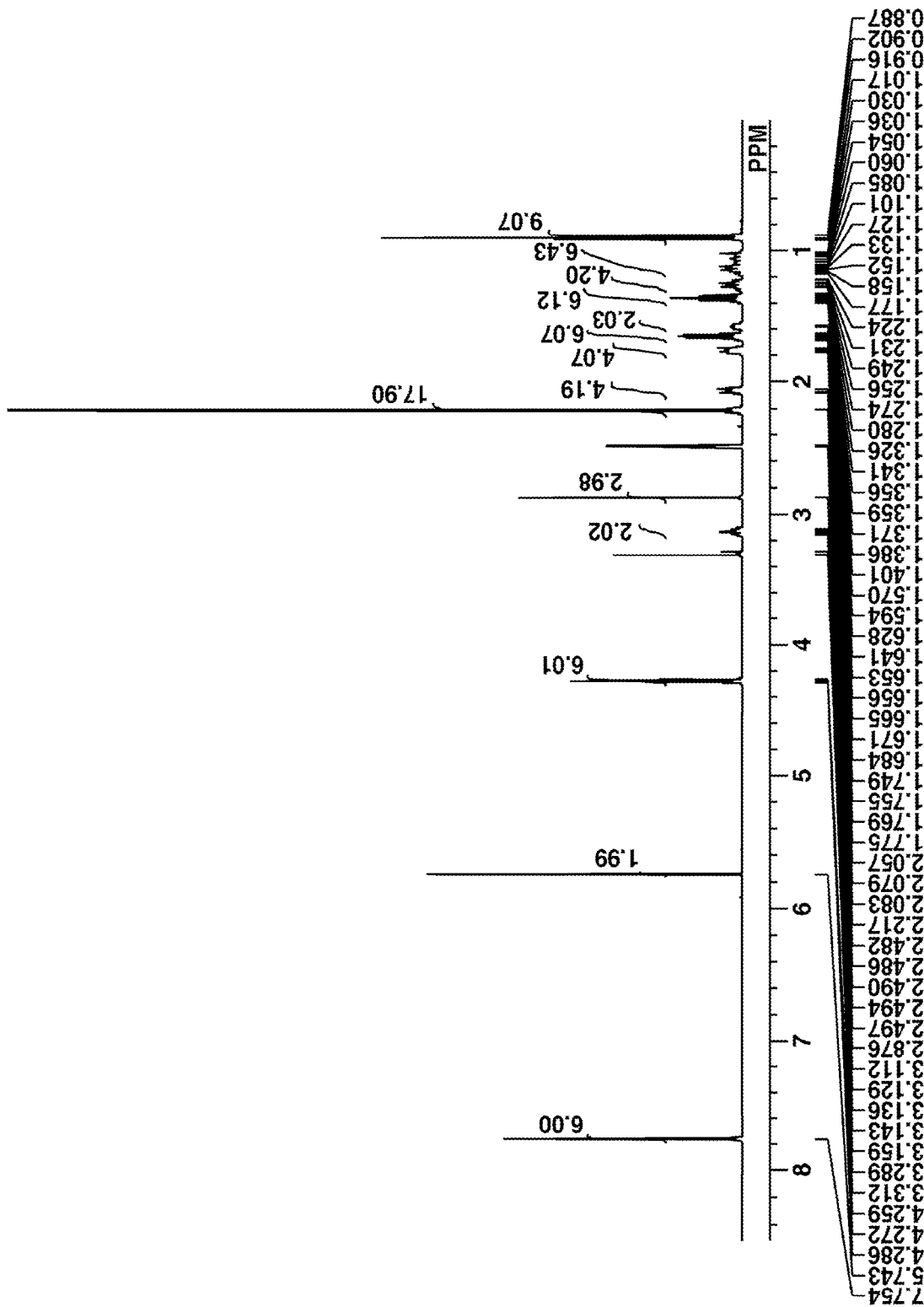
FIG. 5 is a diagram showing the $^1$H-NMR spectrum of sulfonium salt S-5 in Synthesis Example 5.

Sulfonium Salt S-5 was analyzed by spectroscopy, with the data shown below. FIG. 5 is the $^1$H-NMR/DMSO-d$_6$ spectrum of S-5. In the $^1$H-NMR spectroscopy, trace amounts of methylene chloride and water were observed.

IR (D-ATR): 3513, 2959, 2933, 2857, 1762, 1477, 1453, 1387, 1290, 1250, 1189, 1134, 1111, 1066, 1013, 991, 950, 925, 893, 766, 692, 657, 610, 584, 544, 528, 456 cm$^{-1}$ MALDI TOF-MS

Positive M$^+$ 695 (corresponding to $C_{39}H_{51}O_9S^+$)

Negative M$^-$ 385 (corresponding to $C_{14}H_{25}O_6S_3^-$)

Synthesis Example 6

Synthesis of bis(4-tert-butoxycarbonyloxy-3,5-dimethylphenyl)phenylsulfonium chloride (Sulfonium Salt S-6)

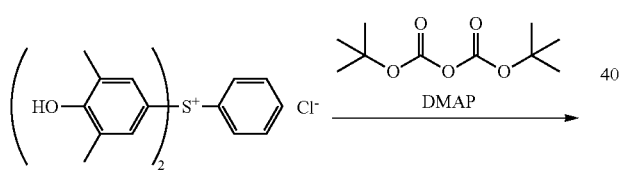

In 75 g of methylene chloride, 20.1 g of bis(4-hydroxy-3,5-dimethylphenyl)-phenylsulfonium chloride, which was synthesized by a well-known method, and 0.6 g of 4-dimethylaminopyridine were dissolved. A solution of 26.2 g of di-tert-butyl dicarbonate in 25 g of methylene chloride was added dropwise thereto. At the end of addition, the solution was stirred at room temperature for 12 hours. After the reaction solution was cooled, 100 g of water was added dropwise to quench the reaction. The organic layer was taken out, washed with water, and concentrated under reduced pressure. Diisopropyl ether was added to the concentrate for recrystallization. The resulting crystals were collected by filtration and dried in vacuum, obtaining 32.2 g (yield 96%) of the target compound, Sulfonium Salt S-6 in powder form.

Figure 6:
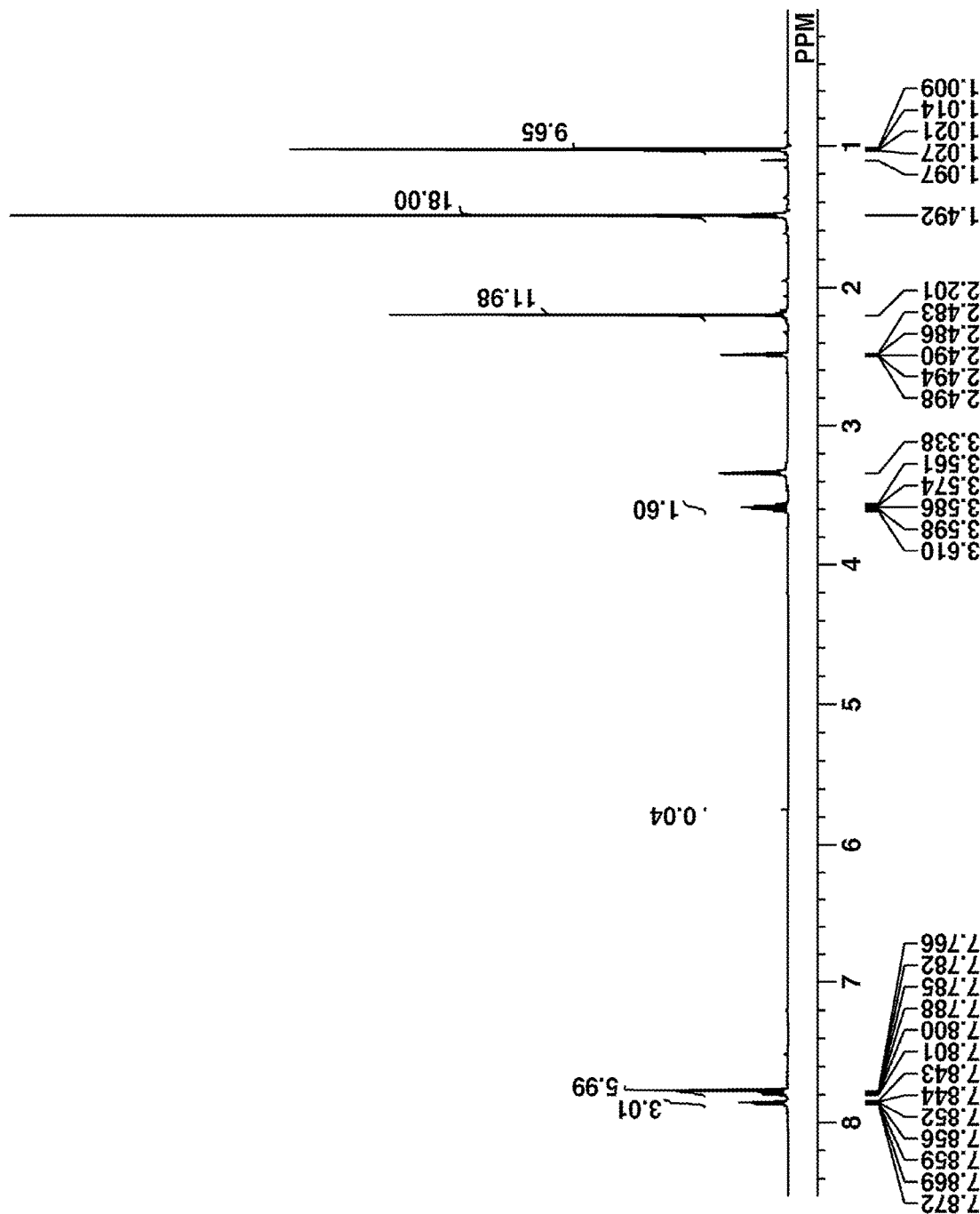
FIG. 6 is a diagram showing the $^1$H-NMR spectrum of sulfonium salt S-6 in Synthesis Example 6.

Sulfonium Salt S-6 was analyzed by spectroscopy, with the data shown below. FIG. 6 is the $^1$H-NMR/DMSO-d$_6$ spectrum of S-6. In the $^1$H-NMR spectroscopy, trace amounts of diisopropyl ether, methylene chloride and water were observed.

IR (D-ATR): 3377, 2977, 2932, 1756, 1626, 1578, 1477, 1446, 1396, 1370, 1272, 1257, 1197, 1143, 1106, 1046, 1012, 896, 861, 806, 781, 751, 685, 578, 523, 494 cm$^{-1}$ MALDI TOF-MS

Positive M$^+$ 551 (corresponding to $C_{32}H_{39}O_6S^+$)

Negative M$^-$ 35 (corresponding to Cl$^-$)

Synthesis Example 7

Synthesis of bis(4-tert-butoxycarbonyloxy-3,5-dimethylphenyl)phenylsulfonium bis(cyclohexanesulfonyl)(methanesulfonyl)methide (Sulfonium Salt S-7)

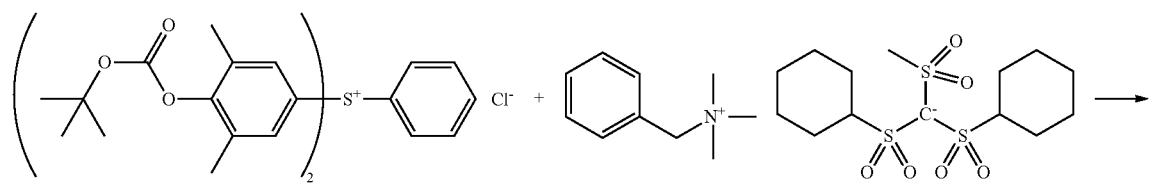

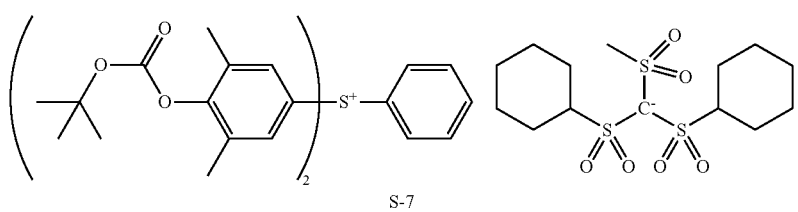

Synthesis was carried out by the same procedure as in Synthesis Example 2 aside from using Sulfonium Salt S-6 instead of tris(4-tert-butoxycarbonyloxy-3,5-dimethyl-phenyl)sulfonium chloride, obtaining 25.4 g (yield 90%) of the target compound, Sulfonium Salt S-7 in powder form.

Figure 7:
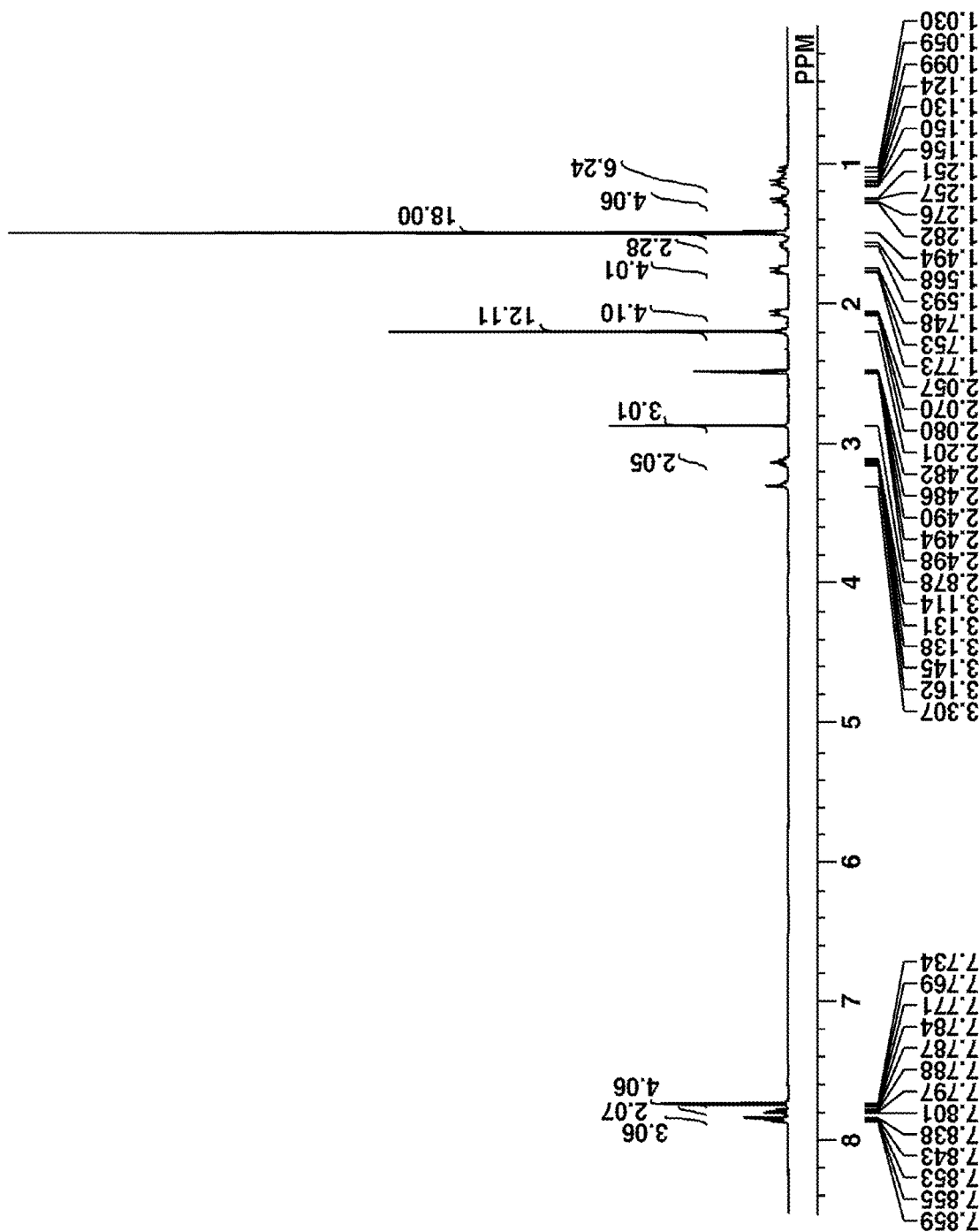
FIG. 7 is a diagram showing the $^1$H-NMR spectrum of sulfonium salt S-7 in Synthesis Example 7.

Sulfonium Salt S-7 was analyzed by spectroscopy, with the data shown below. FIG. 7 is the $^1$H-NMR/DMSO-$d_6$ spectrum of S-7. In the $^1$H-NMR spectroscopy, a trace of water was observed.

IR (D-ATR): 3061, 2977, 2934, 2857, 1757, 1476, 1447, 1397, 1371, 1299, 1282, 1271, 1254, 1202, 1149, 1110, 1100, 1011, 989, 948, 895, 864, 761, 687, 656, 608, 544, 528, 515, 455 cm$^{-1}$

MALDI TOF-MS
Positive M$^+$ 551 (corresponding to $C_{32}H_{39}O_6S^+$)
Negative M$^+$ 385 (corresponding to $C_{14}H_{25}O_6S_3^-$)

Synthesis Example 8

Synthesis of (4-tert-butoxycarbonyloxy-3,5-dimethylphenyl)diphenylsulfonium bromide (Sulfonium Salt S-8)

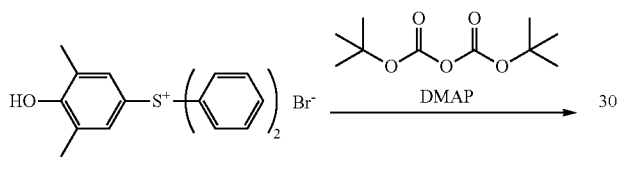

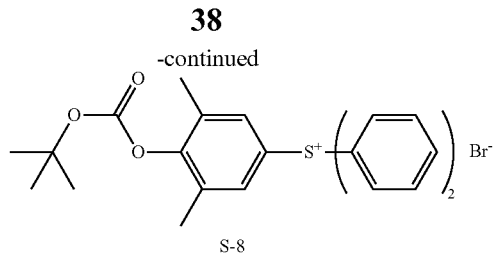

S-8

Synthesis was carried out by the same procedure as in Synthesis Example 6 aside from using (4-hydroxy-3,5-dimethylphenyl)diphenylsulfonium bromide instead of bis(4-hydroxy-3,5-dimethylphenyl)phenylsulfonium chloride, obtaining 15.5 g (yield 79%) of the target compound, Sulfonium Salt S-8 in powder form.

Figure 8:
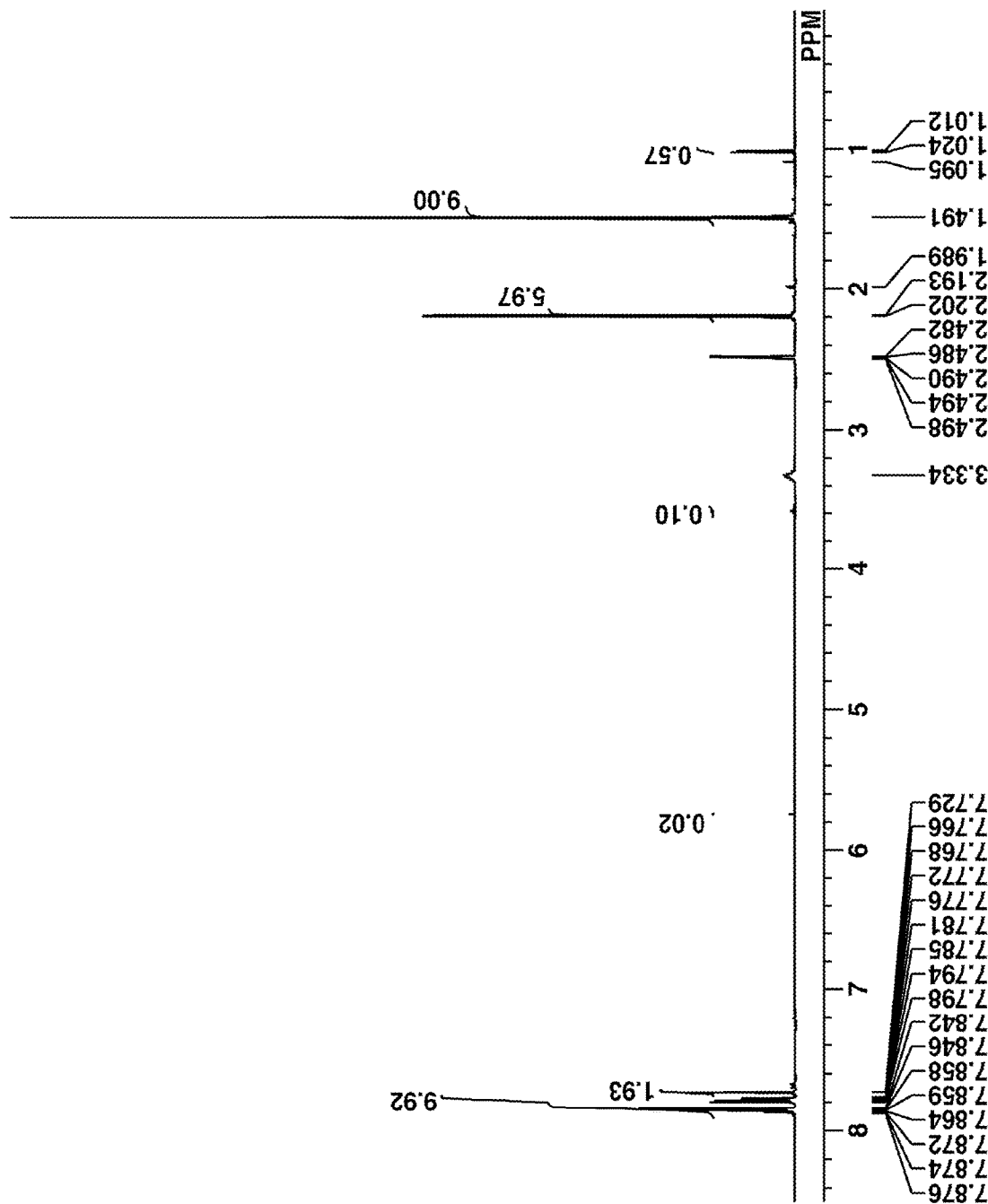
FIG. 8 is a diagram showing the $^1$H-NMR spectrum of sulfonium salt S-8 in Synthesis Example 8.

Sulfonium Salt S-8 was analyzed by spectroscopy, with the data shown below. FIG. 8 is the $^1$H-NMR/DMSO-$d_6$ spectrum of S-8. In the $^1$H-NMR spectroscopy, trace amounts of diisopropyl ether, methylene chloride and water were observed.

IR (D-ATR): 3659, 3408, 3075, 3046, 2982, 1759, 1576, 1475, 1446, 1397, 1370, 1285, 1269, 1256, 1199, 1154, 1109, 1048, 998, 908, 893, 860, 806, 781, 768, 748, 715, 690, 682, 614, 582, 525, 505, 474 cm$^{-1}$

MALDI TOF-MS
Positive M$^+$ 407 (corresponding to $C_{25}H_{27}O_3S^+$)
Negative M$^-$ 79 (corresponding to Br$^-$)

Synthesis Example 9

Synthesis of (4-tert-butoxycarbonyloxy-3,5-dimethylphenyl)diphenylsulfonium bis(cyclohexanesulfonyl)(methanesulfonyl)methide (Sulfonium Salt S-9)

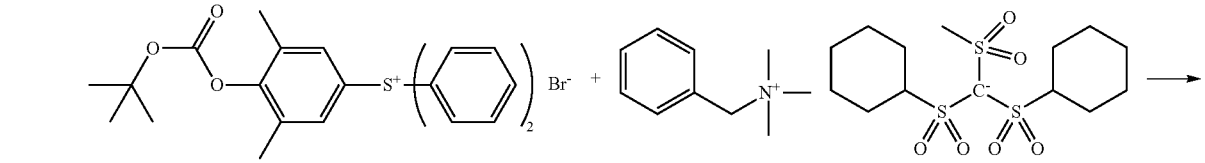

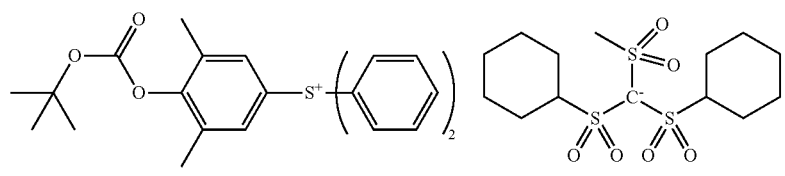

S-9

Synthesis was carried out by the same procedure as in Synthesis Example 2 aside from using Sulfonium Salt S-8 instead of tris(4-tert-butoxycarbonyloxy-3,5-dimethyl-phenyl)sulfonium chloride, obtaining 22.3 g (yield 94%) of the target compound, Sulfonium Salt S-9 in powder form.

Figure 9:
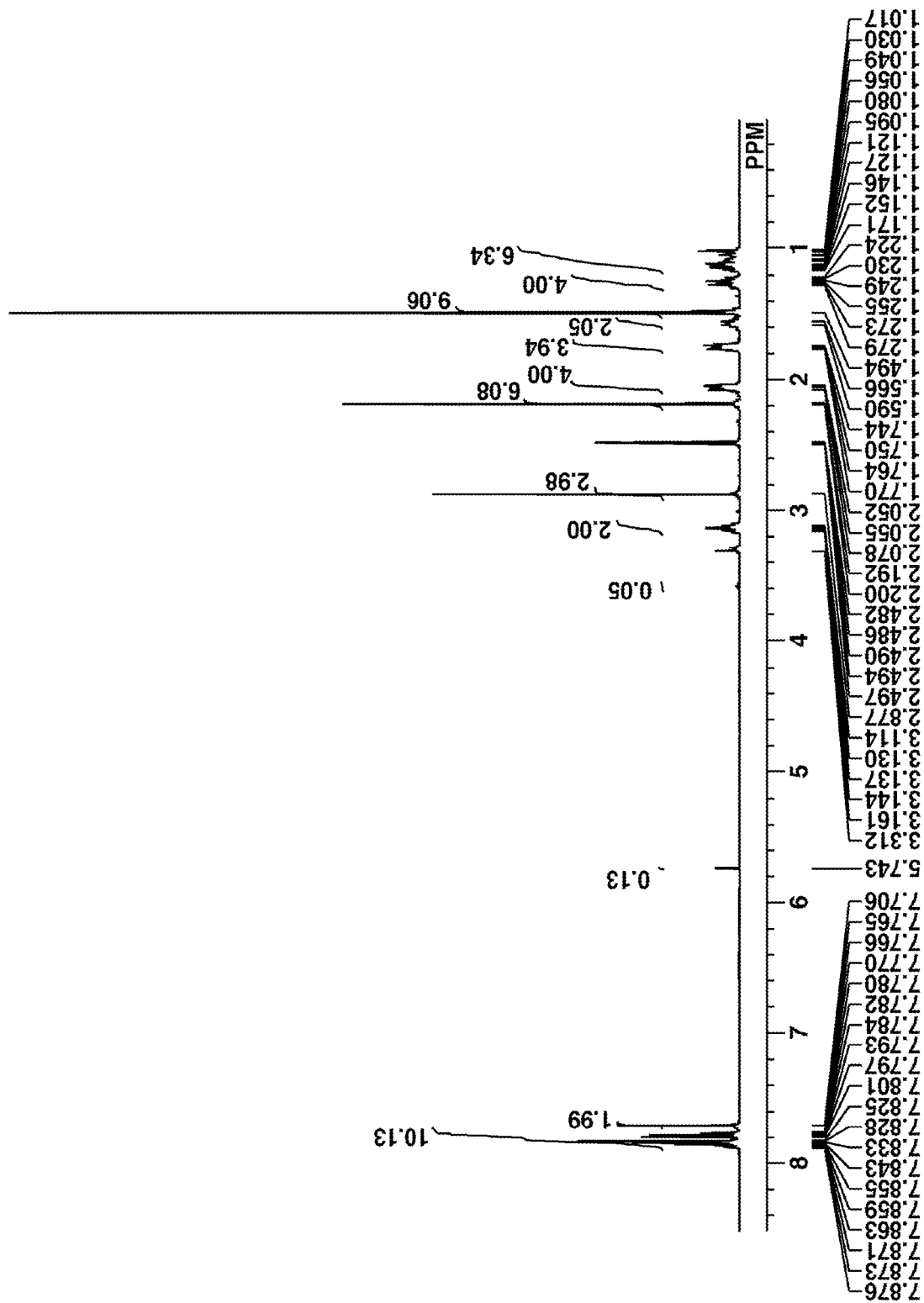
FIG. 9 is a diagram showing the $^1$H-NMR spectrum of sulfonium salt S-9 in Synthesis Example 9.

Sulfonium Salt S-9 was analyzed by spectroscopy, with the data shown below. FIG. 9 is the $^1$H-NMR/DMSO-$d_6$ spectrum of S-9. In the $^1$H-NMR spectroscopy, trace amounts of diisopropyl ether, methylene chloride and water were observed.

IR (D-ATR): 3089, 3064, 2976, 2938, 2856, 1757, 1580, 1478, 1450, 1396, 1371, 1297, 1282, 1253, 1205, 1155, 1136, 1109, 1099, 1009, 989, 947, 895, 865, 748, 682, 656, 607, 585, 545, 529, 514, 472, 456, 423 cm$^{-1}$

MALDI TOF-MS

Positive M$^+$ 407 (corresponding to $C_{25}H_{27}O_3S^+$)
Negative M$^-$ 385 (corresponding to $C_{14}H_{25}O_6S_3^-$)

[2] Synthesis of Base Polymer for Comparative Resist Composition

Comparative Synthesis Example 1

Synthesis of Polymer P-1

In nitrogen atmosphere, 27.8 g of p-hydroxystyrene, 72.2 g of 1-methylcyclopentyl methacrylate, and 6.08 g of dimethyl 2,2'-azobisisobutyrate were dissolved in 155 g of PGMEA. In nitrogen atmosphere and with stirring, the solution was added dropwise to 78 g of PGMEA at 80° C. over 6 hours. At the end of addition, the solution was stirred for 2 hours while maintaining the temperature of 80° C. The solution was cooled to room temperature, after which it was added dropwise to 3,000 g of n-hexane for precipitation. The solid precipitate was filtered and dried in vacuum at 50° C. for 20 hours, obtaining Polymer P-1 in white powder form. Amount 85 g and yield 85%.

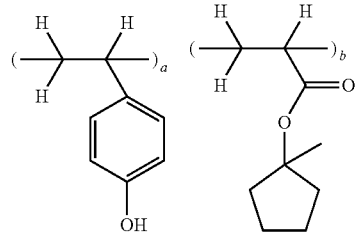

a = 0.35, b = 0.65
Mw = 8,000

Comparative Synthesis Example 2

Synthesis of Polymer P-2

Polymer P-2 was synthesized by the same procedure as in Comparative Synthesis Example 1 aside from changing the type and mixing ratio of monomers.

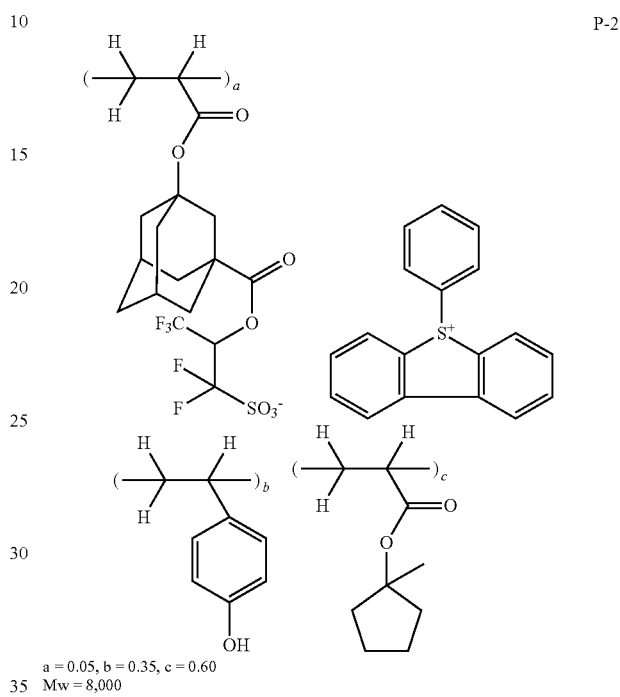

a = 0.05, b = 0.35, c = 0.60
Mw = 8,000

[3] Preparation of Resist Composition

Examples 1-1 to 1-6 and Comparative Examples 1-1 to 1-3

Molecular resist compositions (R-01 to R-06) were prepared by dissolving a sulfonium salt (S-1, S-2, S-3, S-5, S-7, S-9) in a solvent in accordance with the formulation shown in Table 1, and filtering through a Teflon® filter with a pore size of 0.2 μm. Comparative resist compositions (R-07 to R-09) were prepared by mixing a polymer, photoacid generator, sensitivity adjusting agent, surfactant and solvent in accordance with the formulation shown in Table 1, and filtering through a Teflon® filter with a pore size of 0.2 μm.

TABLE 1

| | | Resist composition | Polymer (pbw) | Photoacid generator (pbw) | Sensitivity adjusting agent (pbw) | Surfactant (pbw) | Solvent 1 (pbw) | Solvent 2 (pbw) |
|---|---|---|---|---|---|---|---|---|
| Example | 1-1 | R-01 | — | S-1 (97) | — | — | PGMEA (1500) | DAA (600) |
| | 1-2 | R-02 | — | S-2 (138) | — | — | PGMEA (1500) | DAA (600) |
| | 1-3 | R-03 | — | S-3 (121) | — | — | PGMEA (1500) | DAA (600) |
| | 1-4 | R-04 | — | S-5 (138) | — | — | PGMEA (1500) | DAA (600) |
| | 1-5 | R0-5 | — | S-7 (120) | — | — | PGMEA (1500) | DAA (600) |

TABLE 1-continued

| | Resist composition | Polymer (pbw) | Photoacid generator (pbw) | Sensitivity adjusting agent (pbw) | Surfactant (pbw) | Solvent 1 (pbw) | Solvent 2 (pbw) |
|---|---|---|---|---|---|---|---|
| | 1-6 | R-06 | — | S-9 (101) | — | — | PGMEA (1500) | DAA (600) |
| Comparative Example | 1-1 | R-07 | — | PAG-A (108) | — | — | PGMEA (1500) | DAA (600) |
| | 1-2 | R-08 | P-1 (65) | PAG-B (19) | Q-A (1.3) | SF-1 (0.01) | PGMEA (1500) | DAA (600) |
| | 1-3 | R-09 | P-2 (65) | — | Q-A (1.3) | SF-1 (0.01) | PGMEA (1500) | DAA (600) |

The photoacid generators (PAG-A, PAG-B), sensitivity adjusting agent (Q-A), surfactant (SF-1), and solvents in Table 1 are identified below.
PAG-A: tris(4-tert-butoxycarbonyloxy-3,5-dimethylphenyl)sulfonium triflate
PAG-B: triphenylsulfonium 2-(adamantane-1-carbonyloxy)-1,1,3,3,3-pentafluoropropane-1-sulfonate
Q-A: 2-morpholinoethyl laurate

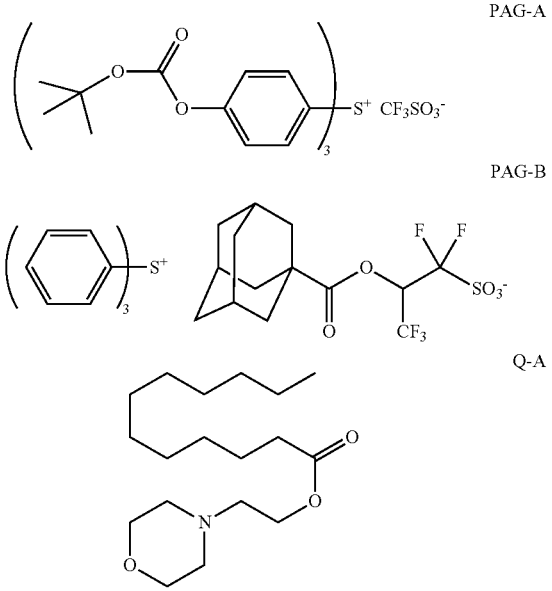

SF-1: PF636 (Omnova Solutions Inc.)
Solvent: PGMEA (propylene glycol monomethyl ether acetate) DAA (diacetone alcohol)

[4] EB Lithography Test

Examples 2-1 to 2-6 and Comparative Examples 2-1 to 2-3

An antireflective coating of 60 nm thick (DUV-42 by Nissan Chemical Industries, Ltd.) was formed on a silicon substrate. Each of the resist compositions (R-01 to R-09) was spin coated on the ARC, and baked on a hotplate at 100° C. for 60 seconds to form a resist film of 50 nm thick. The resist film was exposed to EB on an EB lithography system (ELS-F125, Elionix Co., Ltd., accelerating voltage 125 kV), baked (PEB) on a hotplate at the temperature shown in Table 2 for 60 seconds, and developed in a 2.38 wt % TMAH aqueous solution for 30 seconds to form a pattern. Examples 2-1 and 2-2 showed negative tone performance in that the resist film in the exposed region was left. Comparative Examples 2-2 and 2-3 showed positive tone performance in that the resist film in the unexposed region was left. As a result, line-and-space (LS) patterns of negative or positive tone having a space width of 40 nm and a pitch of 80 nm were obtained. In Comparative Example 2-1, no pattern formation was confirmed. The LS pattern was observed under an electron microscope CD-SEM (CG-5000 by Hitachi High-Technologies Corp.). The LS pattern was evaluated for sensitivity, LWR, and maximum resolution by the following methods. The results are shown in Table 2.

Evaluation of Sensitivity

The optimum dose Eop ($\mu C/cm^2$) which provided a LS pattern with a space width of 40 nm and a pitch of 80 nm was determined and reported as sensitivity.

Evaluation of LWR

For the LS pattern formed by exposure in the optimum dose Eop, the space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Maximum Resolution

The minimum line width (nm) of the LS pattern which remains separate at the optimum dose Eop is reported as maximum resolution.

TABLE 2

| | Resist composition | PEB temp. (° C.) | Eop ($\mu C/cm^2$) | LWR (nm) | Maximum resolution (nm) |
|---|---|---|---|---|---|
| Example | 2-1 | R-01 | 60 | 380 | 4.6 | 28 |
| | 2-2 | R-02 | 60 | 190 | 4.9 | 30 |
| | 2-3 | R-03 | 60 | 360 | 5.0 | 36 |
| | 2-4 | R-04 | 60 | 260 | 4.8 | 32 |
| | 2-5 | R-05 | 60 | 300 | 4.9 | 32 |
| | 2-6 | R-06 | 60 | 380 | 5.1 | 34 |
| Comparative Example | 2-1 | R-07 | 60 | — | — | — |
| | 2-2 | R-08 | 80 | 560 | 6.1 | 40 |
| | 2-3 | R-09 | 80 | 500 | 5.7 | 40 |

It is evident from Table 2 that the molecular resist compositions within the scope of the invention are improved in sensitivity, LWR and maximum resolution over polymeric positive resist compositions when negative patterns are formed by EB lithography and alkaline solvent development.

[5] EUV Lithography Test

Examples 3-1 to 3-6 and Comparative Examples 3-1 to 3-3

Each of the resist compositions (R-01 to R-09) was spin coated on a silicon substrate having a 20-nm coating of silicon-containing spin-on hard mask SHB-A940 (Shin-Etsu Chemical Co., Ltd., silicon content 43 wt %) and prebaked on a hotplate at 100° C. for 60 seconds to form a resist film of 40 nm thick. Using an EUV scanner NXE3300 (ASML, NA 0.33, a 0.9, 90° dipole illumination), the resist film was exposed to EUV through a mask bearing a 1:1 LS pattern having a line width of 22 nm. The resist film was baked (PEB) on a hotplate at the temperature shown in Table 3 for 60 seconds and developed in a 2.38 wt % TMAH aqueous solution for 30 seconds to form a pattern. In Examples 3-1 and 3-2, the resist film in the exposed region was left. In Comparative Examples 3-2 and 3-3, the resist film in the unexposed region was left. As a result, LS patterns of negative or positive tone having a space width of 22 nm and a pitch of 44 nm were obtained. In Comparative Example 3-1, no pattern formation was confirmed. The LS pattern was observed under an electron microscope CD-SEM (CG-5000 by Hitachi High-Technologies Corp.). The LS pattern was evaluated for sensitivity, LWR, and maximum resolution by the following methods. The results are shown in Table 3.

Evaluation of Sensitivity

The optimum dose Eop (mJ/cm$^2$) which provided a LS pattern with a space width of 22 nm and a pitch of 44 nm was determined and reported as sensitivity.

Evaluation of LWR

For the LS pattern formed by exposure in the optimum dose Eop, the space width was measured at longitudinally spaced apart 10 points, from which a 3-fold value (3a) of standard deviation (a) was determined and reported as LWR. A smaller value of 3a indicates a pattern having a lower roughness and more uniform space width.

Evaluation of Maximum Resolution

The minimum line width (nm) of the LS pattern which remains separate at the optimum dose Eop is reported as maximum resolution.

TABLE 3

| | | Resist composition | PEB temp. (° C.) | Eop (mJ/cm2) | LWR (nm) | Maximum resolution (nm) |
|---|---|---|---|---|---|---|
| Example | 3-1 | R-01 | 60 | 30 | 3.0 | 16 |
| | 3-2 | R-02 | 60 | 22 | 3.4 | 18 |
| | 3-3 | R-03 | 60 | 34 | 3.4 | 18 |
| | 3-4 | R-04 | 60 | 24 | 3.0 | 16 |
| | 3-5 | R-05 | 60 | 26 | 3.2 | 16 |
| | 3-6 | R-06 | 60 | 28 | 3.4 | 18 |
| Comparative | 3-1 | R-07 | 60 | — | — | — |
| Example | 3-2 | R-08 | 80 | 52 | 4.8 | 22 |
| | 3-3 | R-09 | 80 | 40 | 3.8 | 20 |

It is evident from Table 3 that as in the case of EB lithography, the molecular resist compositions within the scope of the invention are improved in sensitivity, LWR and maximum resolution over polymeric positive resist compositions when negative patterns are formed by EUV lithography and alkaline solvent development.

Japanese Patent Application No. 2020-161573 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

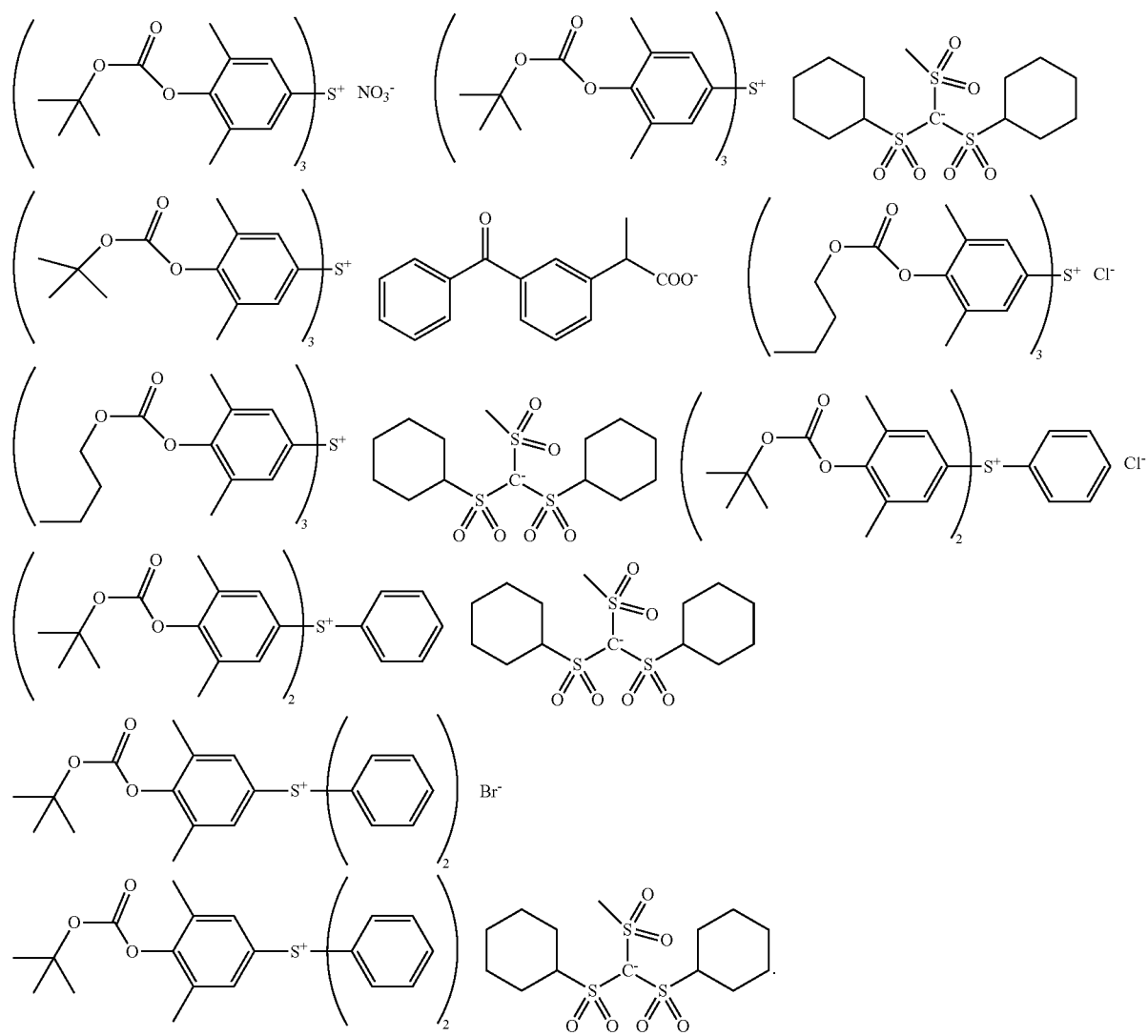

The invention claimed is:

1. A molecular resist composition comprising a sulfonium salt having the formula (1) and an organic solvent, wherein the molecular resist composition does not contain a base polymer,

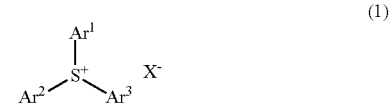

(1)

wherein Ar$^1$, Ar$^2$ and Ar$^3$ are each independently a C$_6$-C$_{20}$ aryl group in which some or all of the hydrogen atoms on its aromatic ring may be substituted by halogen or a C$_1$-C$_{20}$ hydrocarbyl group which may contain a heteroatom, at least one of Ar$^1$, Ar$^2$ and Ar$^3$ is substituted with a group having the formula (1a), (1b) or (1c), any two of Ar$^1$, Ar$^2$ and Ar$^3$ may bond together to form a ring with the sulfur atom to which they are attached,

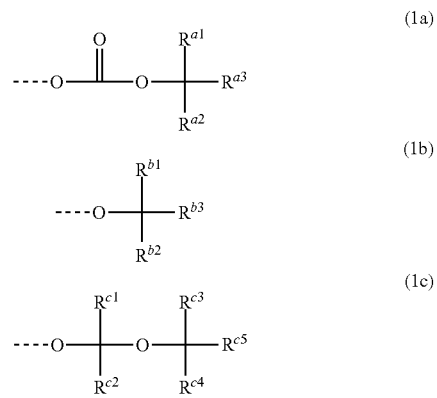

wherein R$^{a1}$, R$^{a2}$ and R$^{a3}$ are each independently hydrogen or a C$_1$-C$_{10}$ hydrocarbyl group; R$^{b1}$, R$^{b2}$ and R$^{b3}$ are each independently a C$_1$-C$_{10}$ hydrocarbyl group, R$^{b1}$ and R$^{b2}$ may bond together to form a ring with the carbon atom to which they are attached; R$^{c1}$ and R$^{c2}$ are each independently hydrogen or a C$_1$-C$_{10}$ hydrocarbyl group, R$^{c3}$, R$^{c4}$ and R$^{c5}$ are each independently a C$_1$-C$_{10}$ hydrocarbyl group, R$^{c3}$ and R$^{c4}$ may bond together to form a ring with the carbon atom to which they are attached; the broken line designates a valence bond, and X$^-$ is an anion, exclusive of a halide ion, BF$_4^-$, PF$_6^-$, SbF$_6^-$ and anions having the following formulae (ex1) to (ex4):

(ex1)

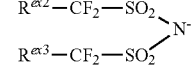

(ex2)

-continued (ex3)

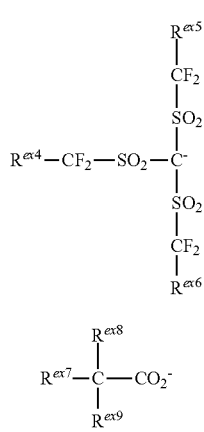

(ex4)

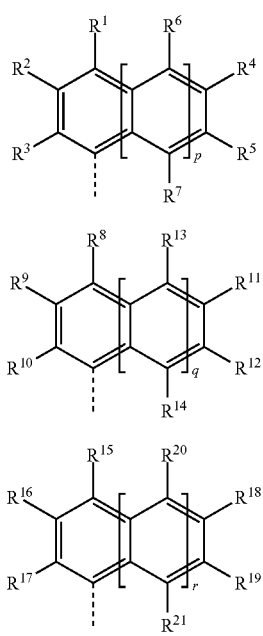

wherein $R^{ex1}$ is halogen or a $C_1$-$C_{40}$ hydrocarbyl group which may contain a heteroatom; $R^{ex2}$, $R^{ex3}$, $R^{ex4}$, $R^{ex5}$ and $R^{ex6}$ are each independently fluorine or a $C_1$-$C_{40}$ hydrocarbyl group which may contain a heteroatom, $R^{ex2}$ and $R^{ex3}$ may bond together to form a ring with the carbon atoms to which they are attached and intervening atoms, $R^{ex4}$ and $R^{ex5}$ may bond together to form a ring with the carbon atoms to which they are attached and intervening atoms; $R^{ex7}$ is halogen, hydroxy or a $C_1$-$C_{40}$ hydrocarbyl group which may contain a heteroatom; $R^{ex8}$ and $R^{ex9}$ are each independently fluorine or trifluoromethyl.

2. The molecular resist composition of claim 1 wherein $Ar^1$, $Ar^2$ and $Ar^3$ are a group having the formula (2), (3) and (4), respectively:

(2)

(3)

(4)

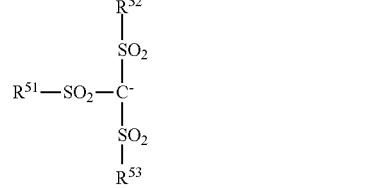

wherein $R^1$ to $R^{21}$ are each independently hydrogen, hydroxy, cyano, halogen, a $C_1$-$C_{20}$ hydrocarbyl group which may contain a heteroatom, or a group having any one of formulae (1a) to (1c), at least one of $R^1$ to $R^{21}$ being a group having any one of formulae (1a) to (1c), p, q and r are each independently 0 or 1, the broken line designates a valence bond.

3. The molecular resist composition of claim 1 wherein $X^-$ is nitrate ion, hydrogensulfate ion, hydrogencarbonate ion, tetraphenylborate ion, or an anion having any one of the formulae (5) to (8):

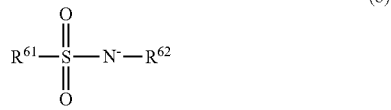

wherein $R^{31}$ is a $C_1$-$C_{40}$ hydrocarbyl group which may contain a heteroatom, exclusive of a hydrocarbyl group in which hydrogen on α-carbon relative to the carboxy group is substituted by fluorine or trifluoromethyl, $R^{41}$ and $R^{42}$ are each independently a $C_1$-$C_{40}$ hydrocarbyl group which may contain a heteroatom, exclusive of a hydrocarbyl group in which hydrogen on α-carbon relative to the sulfonyl group is substituted by fluorine or trifluoromethyl, $R^{41}$ and $R^{42}$ may bond together to form a ring with the sulfur atoms to which they are attached and intervening atom,
$R^{51}$, $R^{52}$ and $R^{53}$ are each independently a $C_1$-$C_{40}$ hydrocarbyl group which may contain a heteroatom, exclusive of a hydrocarbyl group in which hydrogen on α-carbon relative to the sulfonyl group is substituted by fluorine or trifluoromethyl, $R^{51}$ and $R^{52}$ may bond together to form a ring with the sulfur atoms to which they are attached and intervening atom,
$R^{61}$ is fluorine or a $C_1$-$C_{10}$ fluorinated hydrocarbyl group which may contain a hydroxy moiety, ether bond or ester bond, $R^{62}$ is hydrogen or a $C_1$-$C_{20}$ hydrocarbyl group which may contain a hydroxy moiety, ether bond or ester bond, $R^{61}$ and $R^{62}$ may bond together to form a ring with the atoms to which they are attached.

4. The molecular resist composition of claim 1, further comprising a radical trapping agent.

5. The molecular resist composition of claim 1, further comprising a surfactant.

6. A pattern forming process comprising the steps of applying the molecular resist composition of claim 1 onto a substrate to form a resist film thereon, exposing the resist film to high-energy radiation, and developing the exposed resist film in a developer.

7. The process of claim 6 wherein the high-energy radiation is EB or EUV.

8. A molecular resist composition comprising a sulfonium salt selected from the group consisting of the following formulae, and an organic solvent, wherein the molecular resist composition does not contain a base polymer,